(12) United States Patent
Bojanowski

(10) Patent No.: US 10,471,035 B2
(45) Date of Patent: Nov. 12, 2019

(54) COMPOSITIONS AND METHODS FOR USING ESTERS OF MEROTERPENES AND OF OTHER RESVERATROL ANALOGUES

(71) Applicant: Krzysztof Bojanowski, Santa Paula, CA (US)

(72) Inventor: Krzysztof Bojanowski, Santa Paula, CA (US)

(73) Assignee: Sunny BioDiscovery, Santa Paula, CA (US)

(*) Notice: Subject to any disclaimer, the term of this patent is extended or adjusted under 35 U.S.C. 154(b) by 98 days.

(21) Appl. No.: 14/887,308

(22) Filed: Oct. 19, 2015

(65) Prior Publication Data

US 2016/0243069 A1    Aug. 25, 2016

Related U.S. Application Data

(60) Provisional application No. 62/065,762, filed on Oct. 20, 2014.

(51) Int. Cl.

| | | |
|---|---|---|
| *A61K 31/216* | (2006.01) | |
| *A61K 41/00* | (2006.01) | |
| *A61K 8/37* | (2006.01) | |
| *A61K 9/00* | (2006.01) | |
| *A61K 31/618* | (2006.01) | |
| *A61K 31/621* | (2006.01) | |
| *A23L 33/10* | (2016.01) | |
| *A61Q 17/00* | (2006.01) | |
| *A61Q 19/00* | (2006.01) | |
| *A61Q 19/02* | (2006.01) | |
| *A61Q 19/08* | (2006.01) | |
| *A61Q 17/04* | (2006.01) | |
| *A61N 5/06* | (2006.01) | |

(52) U.S. Cl.
CPC ............ *A61K 31/216* (2013.01); *A23L 33/10* (2016.08); *A61K 8/37* (2013.01); *A61K 9/0014* (2013.01); *A61K 31/618* (2013.01); *A61K 31/621* (2013.01); *A61K 41/0066* (2013.01); *A61Q 17/005* (2013.01); *A61Q 19/00* (2013.01); *A61Q 19/02* (2013.01); *A61Q 19/08* (2013.01); *A61K 9/0073* (2013.01); *A61K 2800/522* (2013.01); *A61K 2800/74* (2013.01); *A61N 5/062* (2013.01); *A61Q 17/04* (2013.01)

(58) Field of Classification Search
None
See application file for complete search history.

(56) References Cited

U.S. PATENT DOCUMENTS

| | | |
|---|---|---|
| 8,496,917 B2 | 7/2013 | Chaudhuri |
| 8,529,967 B2 | 9/2013 | Chaudhuri |
| 8,859,021 B2 | 10/2014 | Chaudhuri |
| 2005/0256208 A1 | 11/2005 | Lin |
| 2005/0256209 A1 | 11/2005 | Lin |
| 2007/0202245 A1 | 8/2007 | Gantner |
| 2007/0244203 A1 | 10/2007 | Raul |
| 2009/0137534 A1 | 5/2009 | Chaudhuri |
| 2010/0040696 A1 | 2/2010 | Sente |
| 2010/0189669 A1 | 7/2010 | Hakozaki |
| 2012/0201769 A1 | 8/2012 | Hong |
| 2013/0336902 A1* | 12/2013 | Fernandez Prieto .... A61K 8/42 424/59 |

FOREIGN PATENT DOCUMENTS

| | | |
|---|---|---|
| WO | 2008140673 A1 | 11/2008 |
| WO | 2012105990 A1 | 8/2012 |

OTHER PUBLICATIONS

Adhikari, S., et al., "Antioxidant Activity of Bakuchiol: Experimental Evidences and Theoretical Treatments on the Possible Involvement of the Terpenoid Chain," Chem. Res. Toxicol., 2003, 16(9):1062-1069.

Berridge M. V., et al., "Characterization of the Cellular Reduction of 3-(4,5-dimethylthiazol-2-yl)-2,5-diphenyltetrazolium bromide (MTT): Subcellular Localization, Substrate Dependence, and Involvement of Mitochondrial Electron Transport in MTT Reduction," Arch. Biochem. Biophys., 1993, 303:474-482.

Besaratinia, A., et al., "Rapid repair of UVA-induced oxidized purines and persistence of UVB-induced dipyrimidine lesions determine the mutagenicity of sunlight in mouse cells," FASEB J., 2008, 22(7):2379-92.

Chaudhuri, R. K., et al., "Bakuchiol in the Management of Acne-Affected Skin," Cosmetics & Toiletries Magazine, 2011, 126(7):502-510.

Conte da Frota, M. L., Jr., et al., "In Vitro Optimization of Retinoic Acid-Induced Neuritogenesis and TH Endogenous Expression in Human SH-SY5Y Neuroblastoma Cells by the Antioxidant Trolox," Mol. Cell. Biochem., 2011, 358:325-334.

Harman D., "Origin and evolution of the free radical theory of aging: a brief personal history, 1954-2009," Biogerontology. 2009,10:773-81, doi: 10.1007/s10522-009-9234-2.

Hsu, P. J., et al., "Bakuchiol, an Antibacterial Component of Psoralidium tenuiflorum," Nat. Prod. Res., 2009, 23(8):781-788, doi: 10.1080/14786410902840158.

Iwamura, J., et al., "Cytotoxicity of Corylifoliae fructus. II. Cytotoxicity of Bakuchiol and the Analogues," Yakugaku Zasshi, 1989, 109(12):962-965, (English Absract).

Katsura, H., et al., "In vitro Antimicrobial Activities of Bakuchiol Against Oral Microorganisms," Antimicrob. Agents Chemother., 2001, 45(11):3009-3013.

Madrid, A., et al., "Psoralea glandulosa as a Potential Source of Anticancer Agents for Melanoma Treatment," Int. J. Mol. Sci., 2015, vol. 16:7944-7959.

(Continued)

*Primary Examiner* — David J Blanchard
*Assistant Examiner* — Sarah J Chickos
(74) *Attorney, Agent, or Firm* — Taft Stettinius & Hollister

(57) ABSTRACT

The invention includes compositions and methods of using meroterpene esters for effectively modulating skin cell function and remediating undesirable skin conditions, as well as the use of such compositions in the treatment of systemic diseases, such as cancer and in nutritional, dermatologic and cosmetic applications, through topical and transbuccal delivery as well as by ingestion, injection or inhalation.

19 Claims, 9 Drawing Sheets

(56) References Cited

OTHER PUBLICATIONS

MatTek's OCL-200-EIT protocol p. 20 "Acceptance Criteria for Test Results," 2015.
Ohno, O., et al., "Inhibitory Effects of Bakuchiol, Bavachin, and Isobavachalcone Isolated from Piper Longum on Melanin Production in B16 Mouse Melanoma Cells," Biosci. Biotechnol. Biochem., 2010, 74(7)1504-1506.
Sato K., et al., "Depigmenting Mechanisms of all-trans retinoic acid and retinol on B16 melanoma cells," Biosci. Biotechnol. Biochem., 2008, 72(10)2589-2597.
Reddy, et al. "Novel bisstyryl derivatives of bakuchiol: Targeting oral cavity pathogens" European Journal of Medicinal Chemistry 45 (2010) 3125-3134.
Majeed, et al. "Bakuchiol derivatives as novel and potent cytotoxic agents: A report" European Journal of Medicinal Chemistry 49 (2012) 55-67.

\* cited by examiner

COMPOSITIONS AND METHODS FOR USING ESTERS OF MEROTERPENES AND OF OTHER RESVERATROL ANALOGUES

CROSS-REFERENCE TO RELATED APPLICATION(S)

This application claims the benefit of U.S. Provisional Patent Application Ser. No. 62/065,762, filed on Oct. 20, 2014, the disclosure of which is incorporated by reference herein in its entirety.

BACKGROUND OF THE INVENTION

Meroterpenes are encountered in microorganisms, plants and marine invertebrates and often exhibit substantial toxicity. Some terpenoid compounds, some of which display structural analogy to resveratrol. Bakuchiol is a meroterpene and a resveratrol structural analogue, with great potential for skin-beneficial activities. It is a structural analogue of resveratrol with retinol-like, skin-beneficial functionality, as revealed by comparative gene expression analysis [Chaudhuri R. K., et al., "Bakuchiol: A Retinol-Like Functional Compound Revealed by Gene Expression Profiling and Clinically Proven to Have Anti-Aging Effects," Int. J. Cosmet. Sci. 2014; 36(3):221-230. doi: 10.1111/ics.12117; Chaudhuri, R. K., "Skin Appearance Through Gene Manipulation," U.S. Pat. No. 8,859,021], as well as by its ability to induce same intracellular pathways, such as pro-differentiation, regenerative and pigmentation-inhibitory responses (Sato K, et al., "Depigmenting Mechanisms of all-trans retinoic acid and retinol on B16 melanoma cells," Biosci. Biotechnol. Biochem., October 2008, 72(10):2589-2597; Ohno, O., et al., "Inhibitory Effects of Bakuchiol, Bavachin, and Isobavachalcone Isolated from Piper Longum on Melanin Production in B16 Mouse Melanoma Cells," Biosci. Biotechnol. Biochem., 2010, 74(7):1504-1506; Chaudhuri, R K. "Compositions and Methods for Improving Skin Appearance," U.S. Pat. No. 8,496,917; Li, W. D., "Osteoblasts Proliferation and Differentiation Stimulating Activities of the Main Components of Fructus Psoraleae corylifoliae," J. Phytomedicine, 2014; 21(4):400-405, doi: 10.1016/j.phymed.2013.09.015). Unlike topical retinoids however, bakuchiol possesses direct antimicrobial, antiviral and antifungal activity (Shalita, A. "The Integral Role of Topical and Oral Retinoids in the Early Treatment of Acne," J. Eur. Acad. Dermatol. Venereol., 2001, 15 Suppl. 3:43-49; Katsura, H. et al., "In vitro Antimicrobial Activities of Bakuchiol Against Oral Microorganisms," Antimicrob. Agents Chemother., 2001, 45(11):3009-3013; Hsu, P. J., et al., "Bakuchiol, an Antibacterial Component of Psoralidium tenuiflorum," Nat. Prod. Res., 2009, 23(8):781-788, doi: 10.1080/14786410902840158; Madrid, A., et al., "Antifungal Study of the Resinous Exudate and of Meroterpenoids Isolated from Psoralea glandulosa (Fabaceae)," J. Ethnopharmacol., 2012; 144(3):809-811, doi: 10.1016/j.jep.2012.10.027), including against Propionibacterium acnes (Chaudhuri, R. K., et al., "Bakuchiol in the Management of Acne-Affected Skin," Cosmetics & Toiletries Magazine," 2011, 126(7):502-510); as well as direct anti-oxidant effects (Haraguchi, H., et al., "Antioxidative Components of Psoralea corylifolia (Leguminosae)," Phytother. Res., 2002, 16(6):539-544; Adhikari, S., et al., "Antioxidant Activity of Bakuchiol: Experimental Evidences and Theoretical Treatments on the Possible Involvement of the Terpenoid Chain," Chem. Res. Toxicol., 2003, 16(9):1062-1069; Conte da Froth, M. L. Jr., et al., "All-Trans Retinoic Acid Induces Free Radical Generation and Modulate Antioxidant Enzyme Activities in Rat Sertoli Cells," Mol. Cell Biochem., 2006, 285(1-2):173-179). Another advantage of bakuchiol over retinoids is decreased potential for side effects, possibly linked to the lack of interference with retinoic acid receptors (Chaudhuri R. K., et al., "Bakuchiol: A Retinol-Like Functional Compound Revealed by Gene Expression Profiling and Clinically Proven to Have Anti-Aging Effects," Int. J. Cosmet. Sci. 2014; 36(3):221-230. doi: 10.1111/ics.12117).

Nevertheless, the use of bakuchiol in dermatology and cosmetics may be limited by its brown color, relatively high cytotoxicity (Iwamura, J., et al., "Cytotoxicity of Corylifoliae fructus. II. Cytotoxicity of Bakuchiol and the Analogues," Yakugaku Zasshi, 1989, 109(12):962-965). Bakuchiol is also known to have a high production cost and instability upon long-term storage (Hsu, P. J., et al., "Bakuchiol, an Antibacterial Component of Psoralidium tenuiflorum," Nat. Prod. Res., 2009, 23(8):781-788, doi: 10.1080/14786410902840158) or illumination with UVB light.

SUMMARY OF THE INVENTION

The embodiments disclosed herein relate to compositions and methods of using meroterpene esters for effectively modulating skin cell function and remediating undesirable skin conditions, as well as the use of such compositions in the treatment of systemic diseases, such as cancer and in nutritional, dermatologic and cosmetic applications, through topical and transbuccal delivery as well as by ingestion, injection or inhalation.

DETAILED DESCRIPTION OF THE INVENTION

The present invention is drawn to a series of esterified meroterpene derivatives. In some embodiments, the meroterpene portion of the esterified meroterpene is selected from bakuchiol, hydroxybakuchiol, corylifolin, or a combination thereof. In other embodiments, the ester portion of the esterified meroterpene is selected from a ferulic ester, acetylsalicylic ester, salicylic ester, or a combination thereof. In one embodiment, the meroterpene portion of the esterified meroterpene is bakuchiol and the ester portion is a ferulic ester (abbreviated as SBD.FA.) In another embodiment, the meroterpene portion of the esterified meroterpene is bakuchiol and the ester portion a is salicylic ester (abbreviated as SBD.SE.)

The structure of bakuchiol is:

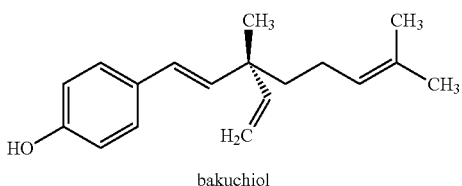 [SMILES: C=C[C@](C)(/C=C/c1ccc(O)cc1)CCC=C(C)C]

bakuchiol

Salicylic acid (a compound known to have anti-pyretic, anti-inflammatory, keratolytic, comedolytic, and bacteriostatic properties) can be esterified with bakuchiol to provide SBD.SE.

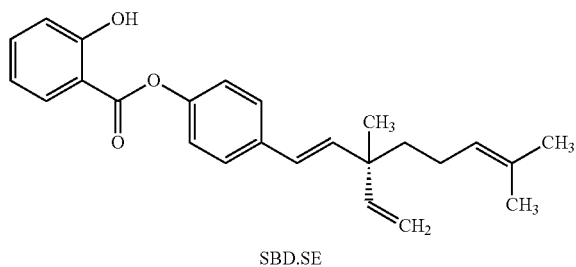 [SMILES: C=C[C@@](C)(/C=C/c1ccc(OC(=O)c2ccccc2O)cc1)CCC=C(C)C ; "SBD.SE"]

SBD.SE

Ferulic acid (a compound known to have anti-oxidant, anti-cancer, whitening and DNA damage—preventive properties) can be esterified with bakuchiol to provide SBD.FA.

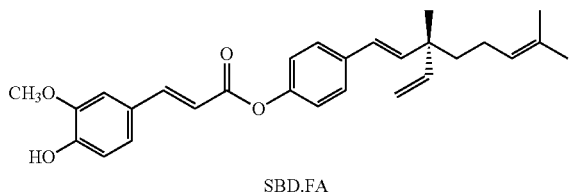

SBD.FA

In some embodiments, the esterified meroterpene derivative, compared to the non-esterified parent compounds, can whiten the color of the esterified compounds, make them less photolabile, decrease their cytotoxicity. In another embodiment, the beneficial bioactivities of the non-esterified parent compounds, such as retinol functionality, antioxidant, anti-cancer, skin-normalizing, whitening and anti-microbial effects, are also retained.

In one embodiment, important for skin care applications, the color of bakuchiol plant extracts with lower content of bakuchiol—such extracts tend to be darker (Chaudhuri R K. Sunscreen Compositions and Methods, U.S. Pat. No. 8,529,967)—is improved (whitened). The purification step normally required to achieve a lighter color is expensive and time/resource-intensive. The esterification of less purified bakuchiol extracts with salicylic acid can lighten them without the aforementioned purification step. In one embodiment, SBD.SE is highly transparent and colorless.

Figure 4:
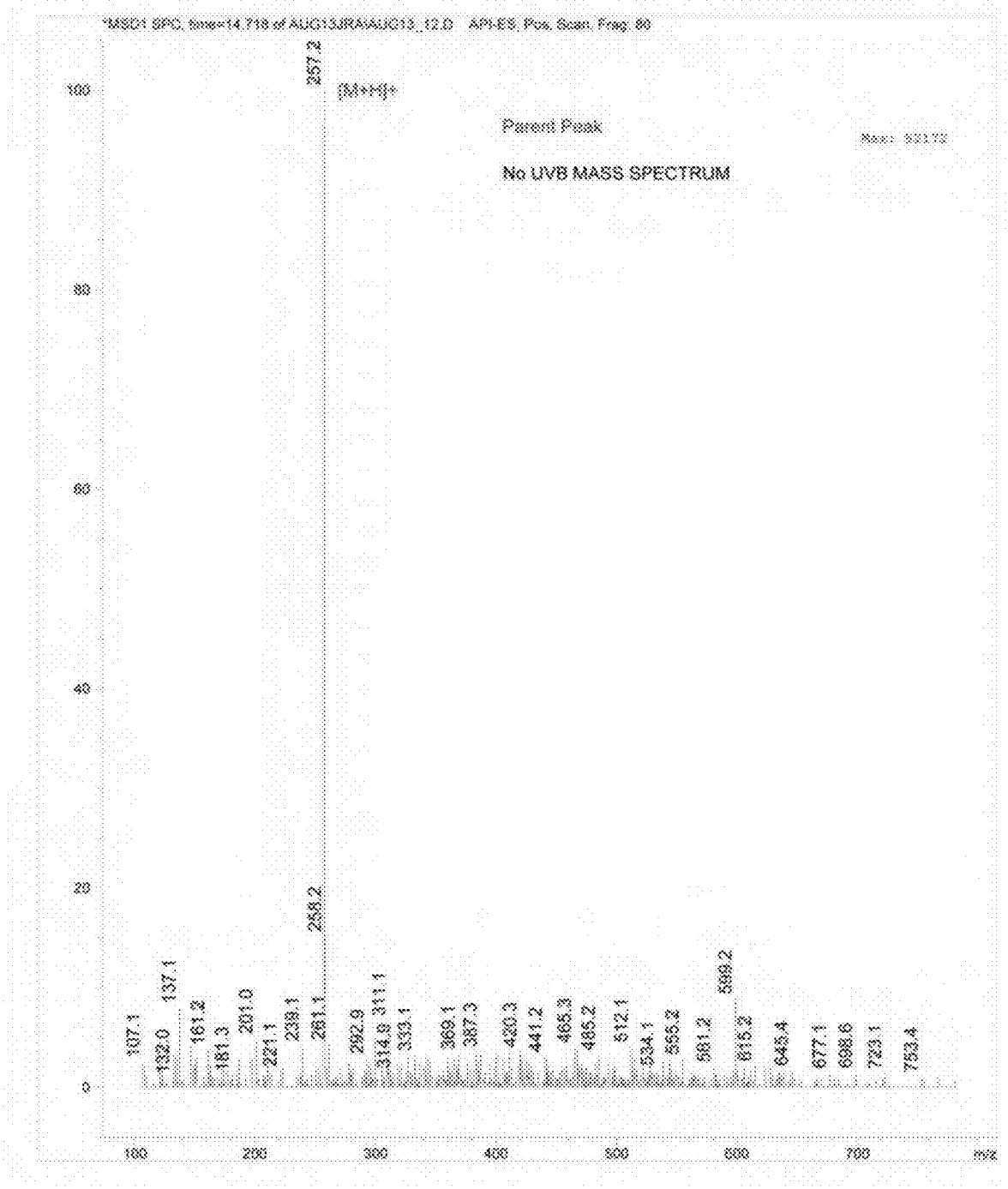
FIG. 4: Mass spectrum of non-irradiated bakuchiol.
Figure 5:
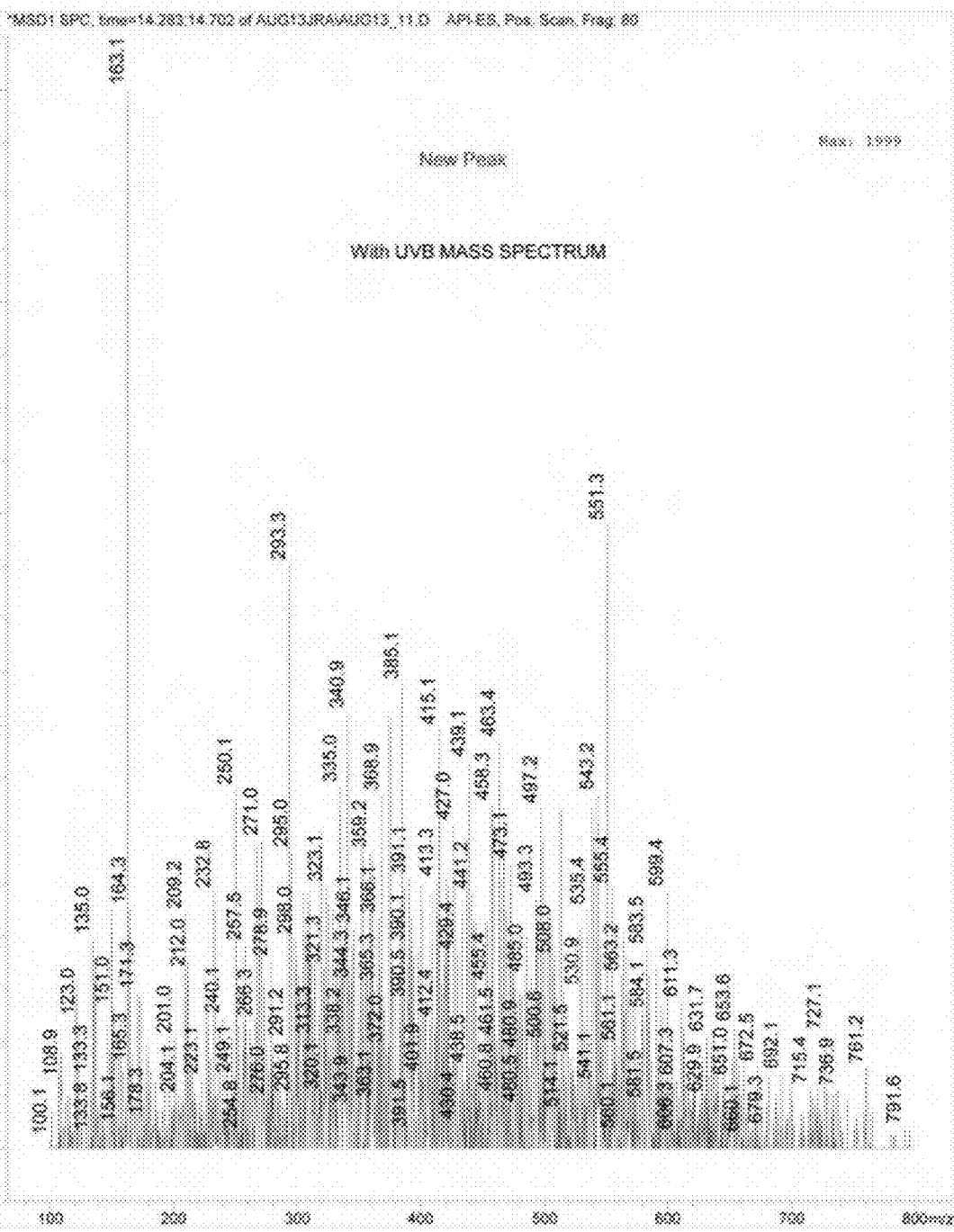
FIG. 5: Mass spectrum of UVB-irradiated bakuchiol.
Figure 6:
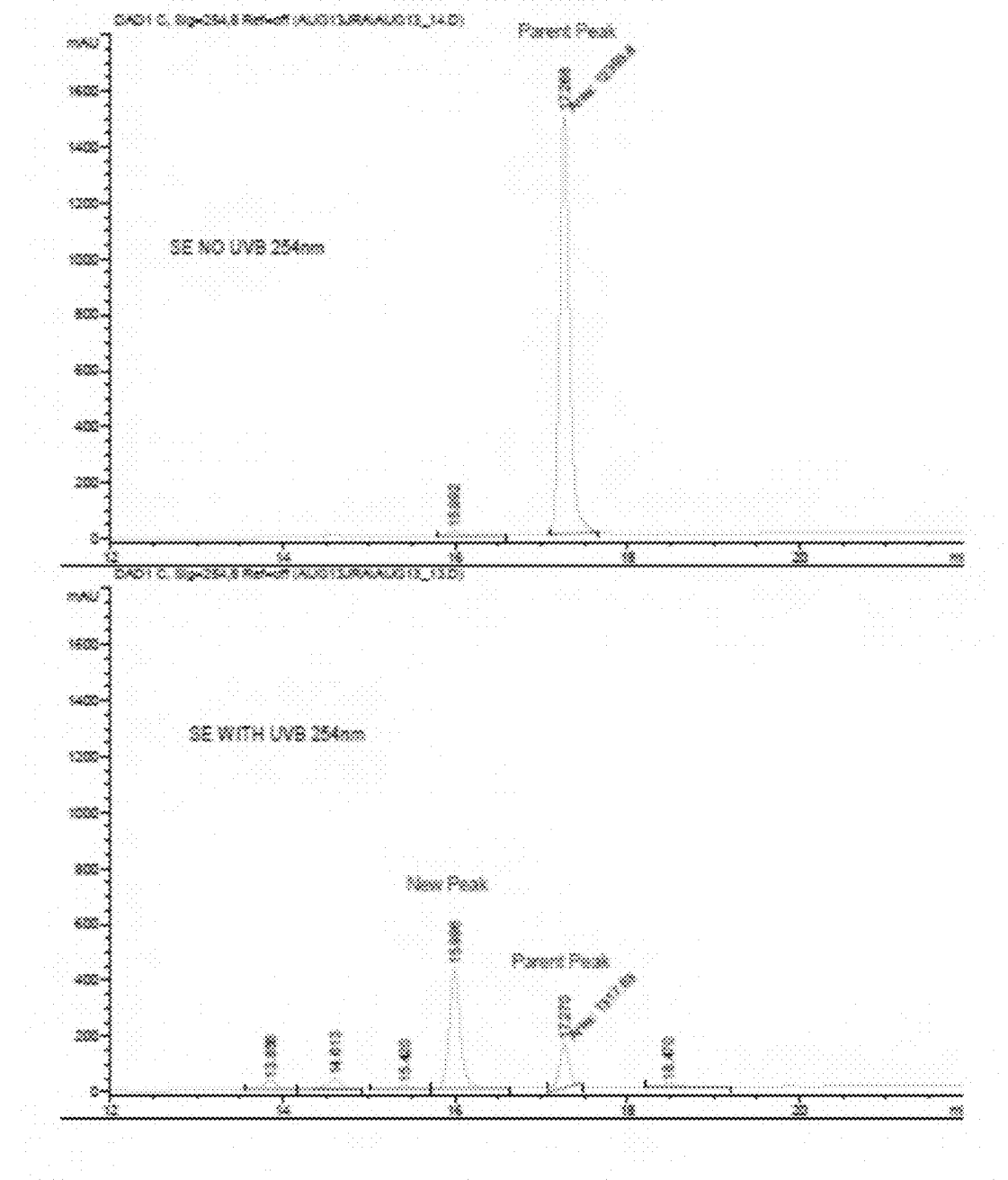
FIG. 6: HPLC chromatogram of non-irradiated and UVB-irradiated SBD.SE, detected at 254 nm.

In some embodiments, the esterified meroterpene derivatives are resistant to degradation by UVB irradiation compared to bakuchiol by itself. Another improvement of physico-chemical properties of bakuchiol by esterification with salicylic acid is the stabilization of its structure, which otherwise is sensitive to UV light. As illustrated in Example 4, bakuchiol, but not its salicylic acid ester, disintegrates under UVB irradiation. This disintegration of bakuchiol (the peak of molecular mass 257) yielding a 163 mass fragment occurs in the junction of its aromatic and aliphatic moieties and is typical for chemicals with aromatic-aliphatic structures. In contrast, surprisingly, the esterification of bakuchiol results in the resistance to the same amount of UVB irradiation, which disrupts bakuchiol. This is a novel and useful finding, given that bakuchiol has been proposed as the active component for improved storage stable emulsive sunscreen formulations (Chaudhuri, R. K., "Sunscreen compositions and methods," U.S. Pat. No. 8,529,967). Salicylic acid ester of bakuchiol will have similar emulsion-stabilizing properties, but will be more stable in storage and under UV light. Thus, esterified meroterpenes in general, and salicylic acid ester of bakuchiol in particular, will provide better solubility of cosmetic ingredients in cosmetic formulations and better skin Another improvement of physico-chemical properties of bakuchiol by esterification with salicylic acid is the stabilization of its structure, which otherwise is sensitive to UV light. The SBD.SE exhibits relative resistance to degradation by UVB irradiation, as compared to bakuchiol by itself. Surprisingly, the SBD.SE retained its retinoic acid functionality as well as anti-microbial and anti-oxidant properties, while its cytotoxicity was substantially decreased. Furthermore, SBD.SE retained its melanogenesis-inhibitory property, while having a differentiation-like effect on the morphology of B16 melanoma cells (Example 1). As illustrated in Example 7, SBD.SE also prevented morphological changes induced in keratinocytes by cytokines IL17A, IL22 and TNF-alpha (Example 8). A very important discovery is that SBD.SE is neither phototoxic (contrarily to some retinoids) nor photolabile (contrarily to retinoic acid and bakuchiol). This disintegration of bakuchiol (FIG. 4, the peak of molecular mass 257) yielding a 163 mass fragment (FIG. 5) occurs in the junction of its aromatic and aliphatic moieties and is typical for chemicals with aromatic-aliphatic structures. The esterification of bakuchiol results in the resistance to the same amount of UVB irradiation, which disrupts bakuchiol [FIG. 2-FIG. 5 (bakuchiol) compare to FIG. 6-FIG. 9 (SBD.SE)]. This is a novel and useful finding, given that bakuchiol has been proposed as the active component for improved storage stable emulsive sunscreen formulations. Salicylic acid ester of bakuchiol will have similar emulsion-stabilizing properties, but will be more stable in storage and under UV light. Thus, esterified meroterpenes in general, and the salicylic acid ester of bakuchiol in particular will provide better solubility of cosmetic ingredients in cosmetic formulations and better skin moisturization than non-esterified meroterpenes in general and bakuchiol in particular.

In other embodiments, the UV-resistance of esterified meroterpenes, such as SBD.SE and SBD.FA may be useful in PUVA therapy—which uses a combination of a drug that makes skin more sensitive to light (such as psoralen) and ultraviolet A light—or other type of light therapy intended to normalize skin condition (such as for eczema or psoriasis). Interestingly, bakuchiol is extracted from plants, which may contain considerable amounts of psoralen. Esterification of bakuchiol extracts naturally enriched in psoralen may constitute a novel PUVA or other light therapeutic modality component with added (retinoid/retinol) functionality. Such benefits are less likely for non-esterified bakuchiol, due to its photolability.

In other embodiments, the esterified meroterpenes may be included in a composition, such as, but not limited to, a pharmaceutical, skin care, or nutrition composition. Pharmaceutical, skin care and nutrition compositions of the present invention include, but are not limited to, solutions, emulsions, and liposome-containing formulations. These compositions may be generated from various components that include, but are not limited to, preformed liquids, self-emulsifying solids and self-emulsifying semisolids.

Pharmaceutical, skin care and nutritional compositions and formulations for topical administration include transdermal patches, ointments, lotions, creams, gels, drops, suppositories, sprays, slow release transbuccal films, liquids and powders. A person of skill in the art would understand that conventional pharmaceutical carriers, aqueous, powder or oily bases, thickeners and the like may be necessary or desirable.

Compositions and formulations for oral intake include powders, granules, aqueous or non-aqueous suspensions or solutions, capsules, sachets or tablets. Thickeners, flavoring agents, diluents, emulsifiers, dispersing aids or binders may be desirable.

Compositions and formulations for parenteral or intraventricular administration include sterile aqueous solutions containing buffers, diluents and other suitable additives such as, but not limited to penetration enhancers and other pharmaceutically acceptable carriers or excipients.

In some embodiments, the pharmaceutical, skin care and nutrition compositions of the present invention may be administered in various ways depending upon whether the treatment is intended to be local or systemic, and upon the area to be treated. Administration may be topical (including skin, mucous membranes, vaginal and rectal delivery), pulmonary, e.g., by inhalation of powders or aerosols, including by nebulizer; intranasal, transoral, epidermal and transdermal, oral or parenteral. Parenteral administration includes intravenous, intra-arterial, subcutaneous, intraperitoneal or intramuscular injection or infusion. The administration can be also per os and transbuccal, with a film or patch.

In other embodiments, the esterified meroterpenes, or compositions comprising said esterified meroterpenes, may be used in effectively modulating skin cell function and remediating undesirable skin conditions, as well as the use of such compositions in the treatment of systemic diseases, such as cancer and in nutritional, dermatologic and cosmetic applications, through topical and transbuccal delivery as well as by ingestion, injection or inhalation. In some embodiments, the esterified meroterpenes, or compositions comprising said esterified meroterpenes, may be used in the treatment of inflammatory and non-inflammatory skin conditions including, but not limited to, hyperpigmentation, psoriasis, dermatitis, eczema, ichthyosis, keratosis, xeroderma, skin aging, skin wrinkling, scleroderma, pachyderma, fibrosis, elephanthiasis, sclerodactyly, elastosis, cancers, and acnes.

EXAMPLES

In view of the above, the following non-limiting examples of compositions and methods of the invention are provided. Nonetheless, the examples are not intended to limit any aspect of the invention to particular mechanism, modes of application, or indications for use.

Example 1: Cytotoxic and Growth Inhibitory Effects on Several Cell Lines by Esterified Meroterpenes The objective of this example is to disclose the experimental results pertaining to the cytotoxicity of SBD.SE and SBD.FA, towards human epidermal keratinocytes (HEK), human dermal fibroblasts (HDF) and mouse melanoma cells, as compared to bakuchiol. Also, the effect of SBD.SE on the epiocular system was investigated. Epiocular system consists of normal, human-derived epidermal keratinocytes, which have been cultured to form a stratified, squamous epithelium similar to that found in the cornea.

Retinoids are used to remediate the effects of photoaging, caused by exposure to solar radiation (Tierney, E. P., Hanke C. W., "Recent Advances in Combination Treatments for Photoaging: Review of the Literature," *Dermatol. Surg.*, 2010, 36:829-40). Therefore, we compared the effect of bakuchiol and SBD.FA on confluent cultures of UVB-irradiated neonatal human dermal fibroblasts (HDF). The total irradiation dose (150mJ/cm2) was biologically relevant, i.e., equivalent to doses received by humans exposed to midday, clear sky, midsummer sun for a moderate period of time (Besaratinia, A., Kim, S. I., Pfeifer, G. P., "Rapid repair of UVA-induced oxidized purines and persistence of UVB-induced dipyrimidine lesions determine the mutagenicity of sunlight in mouse cells," *FASEB J.*, 2008, 22(7): 2379-92). The test materials were added 24 h before irradiation and cultures were terminated 24 h after irradiation. Under these conditions, the cytotoxicity at the highest concentration tested (10 μg/ml) compared to the water-treated control was 36% for bakuchiol and 8% for SBD.FA, as determined by the MTT method (Berridge M. V., Tan A. S., "Characterization of the Cellular Reduction of 3-(4,5-dimethylthiazol-2-yl)-2,5-diphenyltetrazolium bromide (MTT): Subcellular Localization, Substrate Dependence, and Involvement of Mitochondrial Electron Transport in MTT Reduction," *Arch. Biochem. Biophys.* 1993, 303:474-482), using Molecular Devices microplate spectrophotometer MAX190 at 570 nm.

In another experiment with non-irradiated neonatal HDF, which were allowed to form monolayers before the addition of test materials, the concentration of 12.5 μg/ml yielded the cytotoxicity of 39% for bakuchiol, 8% for SBD.FA and 18% for SBD.SE, further substantiating the reduced cytotoxicity of bakuchiol esters as compared to bakuchiol.

For HEK, human neonatal progenitor epidermal keratinocytes (CellnTec, Switzerland) were plated in the presence of different test materials at 6000 cells/well and were grown in CellnTec keratinocyte proliferation medium. Cell numbers were quantified using sulforhodamine B (Voigt, W., "Sulforhodamine B Assay and Chemosensitivity," *Methods Mol. Med.*, 2005; 110:39-48) or MTT method. The results show that SBD.FA is at least 4 times less toxic to HEK than bakuchiol (ED50=1 μg/ml for SBD.FA and 0.25n/ml for bakuchiol). The ED50 dose for SBD.SE is greater than 10 μg/ml, making it at least 40 times less toxic than bakuchiol.

Regarding the mouse melanoma cells (B16F10), 1 μg/ml to 10 μg/ml of SBD.SE inhibited the growth of these cells, preventing them to grow in clusters and detach. Instead, cells cultured in the presence of SBD.SE grew slower and if allowed to reach monolayer, they become growth-arrested due to contact inhibition. This result indicates that SBD.SE may have anti-proliferative and differentiation, and thus anti-tumor effects against melanoma and possibly other cancer types, such as lymphoma. Other retinoids, such as bexarotene, are known to have antineoplastic activity against cancers such as cutaneous T cell lymphoma.

Interestingly, it appeared that SBD.SE and SBD.FA are more growth-inhibitory for B16F10 melanoma cells than for human epidermal keratinocytes. One experiment showed that adult HEK proliferation was not inhibited by 2.5 μg/ml of SBD.SE and inhibited by 21% by 2.5 μg/ml of SBD.FA. Same 2.5 μg/ml dose resulted in the 44% and 53% inhibition of B16F10 melanocyte proliferation by SBD.SE and SBD.FA respectively.

While the growth medium of control (water)-treated cells was substantially darkened during the course of the culture, the medium of SBD.SE-treated cells was completely deprived of melanin, pointing to the whitening potential of SBD.SE. The mechanism of action for this effect may be multifactorial and involve the inhibition of tyroinase and/or melanin secretion by melanocytes.

The effect of SBD.SE was assayed on the EpiOcular™ tissue, using the MatTek (Ashland, Mass.) EpiOcular™ Eye Irritation Test (OCL-200-EIT) protocol.

Based on the "depth of injury" model, the Epiocular EIT is intended to differentiate those materials that are non-irritants (would not require a warning label in the European chemical classification systems) from those that would require labeling as either GHS1 or 2. Consequentially, this test allows to distinguish those materials that would induce no damage or damage limited into the corneal epithelium from those that would damage/destroy the epithelium and continue damage into the stroma.

This protocol utilizes the MTT-based cytotoxicity readout as the experimental endpoint, and thus effectively measures the cytotoxicity of test materials. Biological duplicates are used for all calculations. SBD.SE was tested at 10% (100 mg/ml) in dimethyl isosorbide (DMI). The negative control was type I sterile water and the positive control was neat methyl acetate. The pre-incubation time I was 60 min., preincubation time II—overnight, treatment time—30 min., post-soak is 120 min, incubation time with MTT test was 3 h and the extraction was overnight. The extracted formazan was quantified with Molecular Devices microplate spectrophotometer MAX190 at 570 nm.

The result of this test shows that the viability of the test material was over 60% of the water control, which classifies this test material as non-irritant and non-cytotoxic in this model system. In contrast, the treatment with a positive control—neat methyl acetate—was cytotoxic, as expected, leaving only 44% of cells viable.

In the test, all of the acceptance criteria (see MatTek's EpiOcular™ Eye Irritation Test (OCL-200-EIT) protocol p. 20 "Acceptance Criteria for Test Results") were fulfilled. Namely, OD570 readings for the Negative Control were >1 and <2.6; the viability of Positive Control (neat methyl acetate) tissues was less than 60% of the Negative Control.

Summary:

In all, it can be seen that SBD.SE and SBD.FA are less cytotoxic than bakuchiol under several conditions including against UVB-irradiated neonatal human dermal fibroblasts and human epidermal keratinocytes. Tests against mouse melanoma cells indicates that that SBD.SE may have anti-proliferative and differentiation, and thus anti-tumor effects against melanoma. Further, the whitening potential of SBDE.SE was demonstrated, and while at the same time shown to be a non-irritant.

Example 2: Antioxidant Property Test of Esterified Meroterpenes

ROS (reactive oxygen species) generation as a byproduct occurs in mitochondria, peroxisomes, cytochromes P450, and other cellular elements. Free radicals are inherent parts of cellular respiration and immune defense systems, but are also effectors of many diseases and aging (Harman D. Origin and evolution of the free radical theory of aging: a brief personal history, 1954-2009. Biogerontology. 2009; 10:773-81. doi: 10.1007/s10522-009-9234-2). Each second, trillions of free radicals are generated in our bodies and their tight regulation is essential. Anti-oxidants are important tools of this regulation.

The objective of this experiment was to determine the antioxidant capacity of SBD.SE, using DPPH assay methodology. DPPH (2,2-diphenyl-1-picrylhydrazyl) is a stable free radical. The principle of the DPPH assay uses the reduction of the DPPH radical (purple) to diphenylpicrylhydrazine (yellow) as an indication of free radical scavenging capacity of a given test material (Schenk, G. H., Swieczkowski, N. K., "Colorimetric determination of pyrogallol and 2,6-dimethoxyphenol with diphenylpicrylhydrazyl," Talanta, 1971, 18:230-4). Following the incubation of a test agent with DPPH solution, a reduction in absorbance at 520 nm compared to control is indicative of DPPH-scavenging. The degree of DPPH scavenging activity is expressed as % water control. Table 6 shows that both SBD.SE and SBD.FA are free radical scavengers, with activity comparable to bakuchiol.

Summary

Antioxidant properties of SBD.SE and SBD.FA has been demonstrated by DPPH scavenging, where their activity as free radical scavengers is comparable to bakuchiol.

Example 3: Demonstration of Retinoic Acid Functionality

Figure 1:
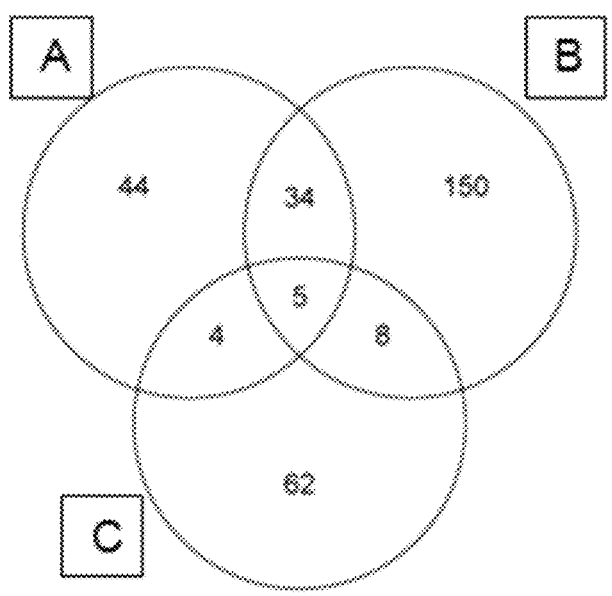
FIG. 1: Venn diagram indicating probe sets significantly modulated by SBD.SE, ATRA, and a compound without retinol functionality.
Figure 2:
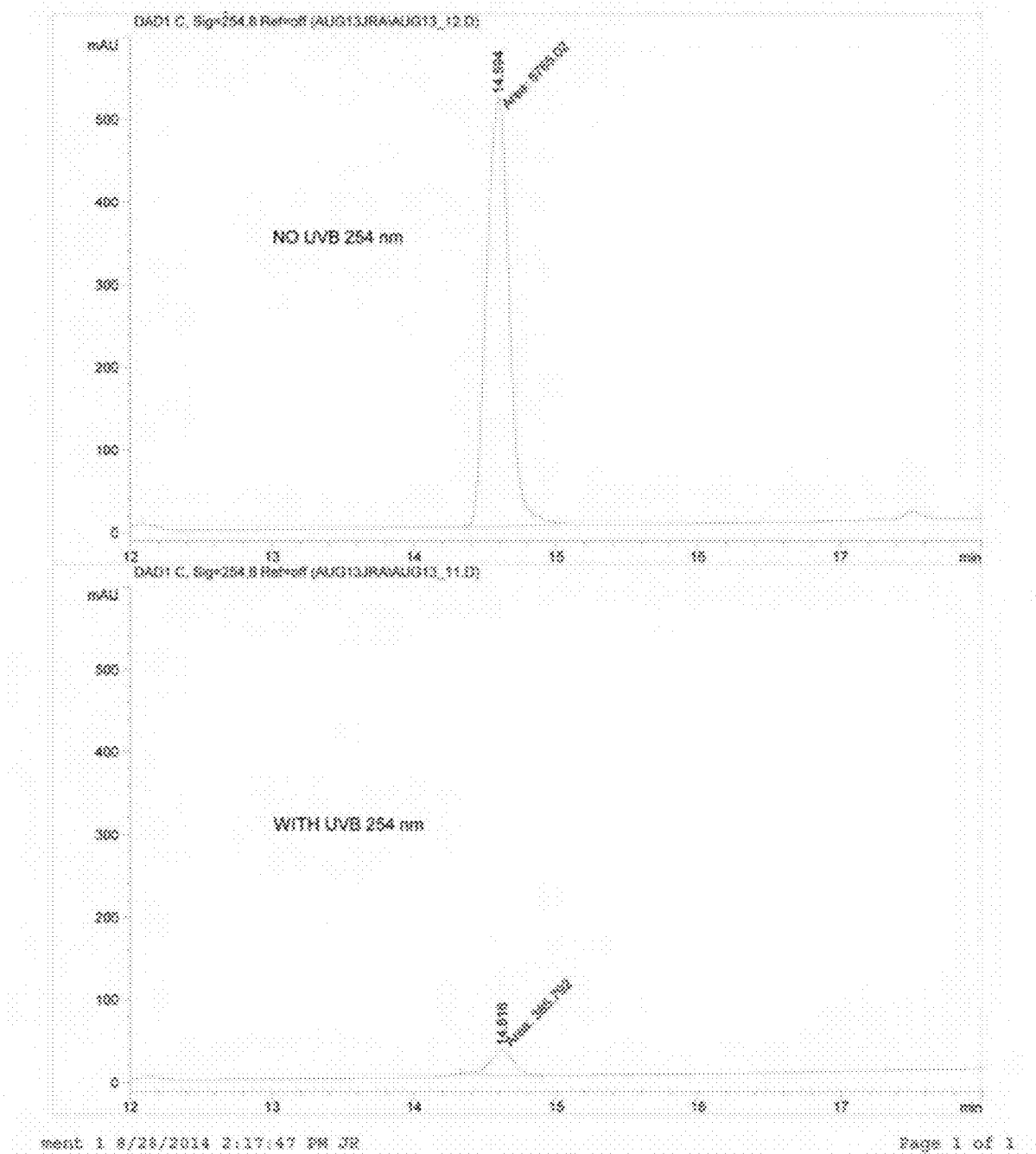
FIG. 2: HPLC chromatogram of non-irradiated and UVB-irradiated bakuchiol, detected at 254 nm.

This example demonstrates the retinoic acid functionality of SBD.SE. IL17A/IL22/TNFalpha-treated keratinocytes were incubated with either water control or with SBD.SE (10 μg/ml), ATRA (all-trans retinoic acid, 0.25 μM) or with another compound without retinol functionality (Compound C), tested in parallel for potential effect on psoriasis. At the end of the incubation, gene expression modulation vs. vehicle control was quantified by DNA microarrays. The Venn diagram (FIG. 1) indicates that while over 77% of probe sets significantly modulated by SBD.SE are also modulated by ATRA, only 12% of the compound C probes are similarly modulated with ATRA, although both compounds have activity consistent with anti-psoriatic therapy. This result demonstrates that Compound A (SBD.SE) but not compound C is a functional retinoid analogue.

The Venn diagram (FIG. 1) showing probe sets unique and common between the three comparisons against the vehicle control [A: SBD.SE; B: ATRA; C: retinoid-unrelated compound with anti-psoriatic activity). Selected probe sets had a fold change of 2 or greater with the added constraint that the average expression for one of the two groups was 25 or greater. This prevents from selecting large fold changes based on small numbers. This statistical analysis of Affymetrix GeneChip™ data was based on GeneChip™ Human U133 Plus 2.0 microarrays that were processed using the IVT Express kit.

Furthermore, the biological processes affected by ATRA and SBD.SE in the above-described experiment were compared. TABLE 1 shows the biological pathways most significantly down-regulated by ATRA and SBD.SE in cytokine-induced psoriatic keratinocytes. Four of these processes (type I interferon—mediated signaling pathway, response to type I interferon, immune response and cellular response to cytokine stimulus) are common to ATRA and SBD.SE, further pointing to the mechanistic analogy in down-regulating the cytokine-driven inflammatory responses in the skin between the 2 compounds. Importantly, this analogy does not extend to morphogenic processes, whose down-regulation is associated with teratogenic effects of ATRA. Table 1 shows that at least 7 morphogenic/developmental pathways were down-regulated by ATRA and none by SBD.SE. Therefore, it may be concluded that SBD.SE is a functional analogue of ATRA with no teratogenic potential.

TABLE 1

| \multicolumn{3}{c|}{Biological processes (BP) in psoriasiform keratinocytes decreased by optimal non-toxic dose of ATRA (0.1 µg/ml)} | \multicolumn{3}{c}{Biological processes (BP) in psoriasiform keratinocytes decreased by the optimal non-cytostatic dose of bakusylan (SBD.SE) (10 µg/ml)} |

| GOBPID | P value | BP Term | GOBPID | P value | BP Term |
|---|---|---|---|---|---|
| GO: 0060337 | 4.02E−12 | type I interferon-mediated signaling pathway | GO: 0006695 | 3.89E−13 | cholesterol biosynthetic process |
| GO: 0034340 | 5.82E−12 | response to type I interferon | GO: 0046165 | 2.6E−11 | alcohol biosynthetic process |
| GO: 0051607 | 6.25E−10 | defense response to virus | GO: 1901615 | 4.2E−10 | organic hydroxy compound metabolic process |
| GO: 0043901 | 1.98E−06 | negative regulation of Multi-organism process | GO: 0006694 | 5.07E−10 | steroid biosynthetic process |
| GO: 0006955 | 8.51E−06 | immune response | GO: 0060337 | 8.58E−09 | type I interferon-mediated signaling pathway |
| GO: 0045071 | 1.09E−05 | negative regulation of viral genome replication | GO: 0034340 | 9.73E−09 | response to type I interferon |
| GO: 0060333 | 2.19E−05 | interferon-gamma-mediated signaling pathway | GO: 0008299 | 4.09E−08 | isoprenoid biosynthetic process |
| GO: 0032501 | 3.02E−05 | multicellular organismal process | GO: 0006639 | 9.16E−07 | acylglycerol metabolic process |
| GO: 0010033 | 4.64E−05 | response to organic substance | GO: 0051607 | 2.09E−06 | defense response to virus |
| GO: 0035457 | 8.19E−05 | cellular response to interferon-alpha | GO: 0046460 | 2.52E−06 | neutral lipid biosynthetic process |
| GO: 0051270 | 8.3E−05 | regulation of cellular component movement | GO: 0051707 | 8.35E−06 | response to other organism |
| GO: 0070887 | 8.46E−05 | cellular response to chemical stimulus | GO: 0019432 | 2.33E−05 | triglyceride biosynthetic process |
| GO: 0016525 | 9.33E−05 | negative regulation of angiogenesis | GO: 0044255 | 3.93E−05 | cellular lipid metabolic process |
| GO: 0002688 | 0.00013 | regulation of leukocyte chemotaxis | GO: 0044710 | 4.04E−05 | single-organism metabolism |
| GO: 0034341 | 0.000196 | response to interferon-gamma | GO: 0006955 | 4.4E−05 | immune response |
| GO: 0065007 | 0.000244 | biological regulation | GO: 0010499 | 0.000137 | proteasomal ubiquitin-independent protein catabolism |
| GO: 0050792 | 0.000249 | regulation of viral process | GO: 0071616 | 0.000355 | acyl-CoA biosynthetic process |
| GO: 0060585 | 0.000264 | positive regulation of prostaglandin-endoperoxide synthase activity | GO: 0048661 | 0.000393 | positive regulation of smooth muscle cell proliferation |
| GO: 1901342 | 0.000267 | regulation of vasculature development | GO: 0009991 | 0.000487 | response to extracellular stimulus |
| GO: 0072358 | 0.000267 | cardiovascular system development | GO: 0016042 | 0.000747 | lipid catabolic process |
| GO: 0048729 | 0.00031 | tissue morphogenesis | GO: 0045445 | 0.000858 | myoblast differentiation |
| GO: 0001655 | 0.000383 | urogenital system development | GO: 0051591 | 0.001067 | response to cAMP |
| GO: 0040012 | 0.000469 | regulation of locomotion | GO: 0046503 | 0.001406 | glycerolipid catabolic process |

TABLE 1-continued

| Biological processes (BP) in psoriasiform keratinocytes decreased by optimal non-toxic dose of ATRA (0.1 µg/ml) | | | Biological processes (BP) in psoriasiform keratinocytes decreased by the optimal non-cytostatic dose of bakusylan (SBD.SE) (10 µg/ml) | | |
|---|---|---|---|---|---|
| GOBPID | P value | BP Term | GOBPID | P value | BP Term |
| GO: 0048705 | 0.000747 | skeletal system morphogenesis | GO: 0019433 | 0.001466 | triglyceride catabolic process |
| GO: 0000462 | 0.000773 | maturation of SSU-rRNA from tricistronic rRNA transcript (SSU-rRNA, 5.8S rRNA | GO: 0046461 | 0.001466 | neutral lipid catabolic process |
| GO: 0048646 | 0.000778 | anatomical structure formation involved in morphogenesis | GO: 0045017 | 0.001771 | glycerolipid biosynthetic process |
| GO: 0060700 | 0.000783 | regulation of ribonuclease activity | GO: 0043330 | 0.001927 | response to exogenous dsRNA |
| GO: 0008544 | 0.000803 | epidermis development | GO: 0035383 | 0.001987 | thioester metabolic process |
| GO: 0071345 | 0.00091 | cellular response to cytokine stimulus | GO: 0071345 | 0.001996 | cellular response to cytokine stimulus |

When the genes modulated by ATRA and SBD.SE were matched with 153 gene expression experiments relevant to skin [GOE Series (GSE) and GEO Platforms (GPL) from the Gene Expression Omnibus—GEO—a public functional genomics data repository], ATRA returned same directionality as SBD.SE in 57% of them, while only 2% were modulated in the opposite direction and the rest was not affected (Table 2; stats cut off +/−0.05). This indicates, again, that SBD.SE has retinoid—like functionality, although in a more narrow spectrum.

One of common features between retinoic acid and SBD.SE was gene regulation consistent with increased TERT activity (GSE experiment vitro129, not shown). This is further confirmed by a separate experiment described below, where SBD.SE was compared to retinol palmitate (table 3, GSE experiment vitro129).

Further analysis of the DNA microarray data from the above-mentioned experiment demonstrates that SBD.SE inhibits the expression of the hormone-sensitive lipase by about 70%. Retinoids, such as etretinate interact with lipid metabolism, and may decrease lipase. Hormones are known to be involved in pathogenesis of acne. Bacteria *Propionibacterium acnes* (*P. acnes*) secrete and utilize lipase in the skin—an activity well known to aggravate acne and lipase decrease has been beneficial in *acnes*. There is correlation between *Propionibacterium acnes* biotypes, lipase activity and rash degree in acne patients (Higaki S, Kitagawa T, Kagoura M, Morohashi M, Yamagishi T. Correlation between *Propionibacterium acnes* biotypes, lipase activity and rash degree in acne patients. J Dermatol. 2000 August; 27(8):519-22). Retinoids, such as etretinate interact with lipid metabolism, and may decrease lipase. Sebaceous glands in skin release sebum, an oily combination of lipids that helps retain moisture. This sebum is broken down by bacteria on the surface of the skin, which contributes to body odor and can be exacerbated by hormonal changes, decreased antioxidant defenses and increased stress. In younger people, skin's natural antioxidant defenses work to prevent these fatty acid breakdown products from being oxidized by the air and turned into other chemicals. Older skin has fewer antioxidants. The results is an accumulation of oxidized substances including the particularly odiferous nonenal. One of the novel aspects of SBD.SE is that its lipase inhibition together with its antioxidant and antimicrobial activity may be very useful in preventing microbial infections, dry skin and body odors.

Furthermore, there is a strong correlation (stat=0.123, p=7.2exp-10) between genes up-regulated in keratinocytes by SBD.SE in the experiment described above and by retinoic acid in an independent experiment ID vitro 58 (GSE22298/GPL571).

Furthermore, when the genes modulated by retinol palmitate and SBD.SE in UVA-irradiated epidermal substitutes cultured on adult fibroblast monolayer were matched with 146 gene expression experiments relevant to skin [GOE Series (GSE) and GEO Platforms (GPL) from the Gene Expression Omnibus—GEO—a public functional genomics data repository], retinol palmitate returned same directionality as SBD.SE in 38% of them (Table 3 (below); stats cut off +0.05 to −0.05). Interestingly, as reported in Table 4 (below), retinol palmitate had some undesirable effects (for example inverse gene regulation to some anti-psoriatic drugs) and SBD.SE had some desirable ones (for example inverse gene regulation in certain cancerous conditions and matching gene regulation with anti-psoriasis drugs), which both compounds didn't share.

Importantly, SBD.SE was found to decrease the expression of genes, which were increased by UVA and UVB irradiation in reference experiments (Table 5, below).

Summary:

SBD.SE shared gene regulation consistent with increased TERT activity, and has been demonstrated to be a functional analogue of trans retinoic acid. Further, genes modulated by trans retinoic acid and SBD.SE were matched with 153 gene expression experiments relevant to skin, where the same directionality was observed in 57% of them, while only 2% were modulated in the opposite direction. Thus, the retinoic acid functionality of SBD.SE has been demonstrated.

TABLE 2

Table 2. Skin - relevant gene expression comparisons from Gene Expression Omnibus (GEO), matched (significantly correlated or significantly inversely correlated) with genes down-regulated by both - retinoic acid AND SBD.SE. (GSE: GEO Series; GPL: GEO Platforms; stats between −0.05 and 0.05 considered not significant match).

| Experiment ID | GOE Series (GSE)/GEO Platform (GPL) Label | ATRA Stat | ATRA FDR | SBD.SE Stat | SBD.SE FDR |
|---|---|---|---|---|---|
| esnp10 | rs610604 (TNFAIP3/6) | −0.109 | 0.000 | −0.24 | 0.000 |
| esnp21 | rs12586317 (NFKBIA/14) | 0.091 | 0.000 | 0.249 | 0.000 |
| esnp23 | rs1008953 (SDC4/20) | −0.069 | 0.006 | −0.09 | 0.058 |
| esnp32 | rs7007032 (CSMD1/8) | 0.053 | 0.034 | 0.089 | 0.071 |
| esnp34 | rs13260637 (CSMD1/8) | 0.06 | 0.016 | 0.216 | 0.000 |
| esnp39 | rs33980500 (TRAF3IP2/6) | 0.075 | 0.003 | 0.278 | 0.000 |
| esnp40 | Deletion (LCE3/1) | −0.078 | 0.001 | −0.1 | 0.046 |
| esnp42 | rs4112788 (LCE3/1) | −0.084 | 0.001 | −0.12 | 0.011 |
| esnp43 | rs842636 (REL/2) | 0.058 | 0.021 | 0.108 | 0.028 |
| esnp5 | rs6887695 (IL12B/5) | 0.083 | 0.001 | 0.117 | 0.018 |
| vitro1 | keratinocytes IL1 -VS- keratinocytes untreated (GSE9120/GPL571) | 0.116 | 0.000 | 0.303 | 0.000 |
| vitro106 | HaCaT keratinocytes ZNF750 RNAi- VS-HaCaT keratinocytes control (GSE38039/GPL6244) | 0.053 | 0.038 | 0.14 | 0.004 |
| vitro110 | reconstituted epidermis STAU RNAi- VS-reconstituted epidermis control (GSE40122/GPL570) | 0.134 | 0.000 | 0.073 | 0.148 |
| vitro112 | keratinocytes phevalin -VS- keratinocytes untreated (GSE32920/GPL571) | −0.073 | 0.009 | 0.103 | 0.062 |
| vitro121 | keratinocytes NFX1-123 overexpression -VS- keratinocytes control (GSE43082/GPL10558) | −0.072 | 0.004 | −0.13 | 0.006 |
| vitro124 | keratinocytes SP60125 SB203580 PD98059 24/48 HRS -VS- keratinocytes untreated (GSE50591/GPL571) | −0.078 | 0.005 | −0.11 | 0.046 |
| vitro126 | keratinocytes SB20358 1/4 HRS -VS- keratinocytes untreated (GSE50591/GPL571) | −0.119 | 0.000 | −0.13 | 0.019 |
| vitro129 | keratinocytes N/Tert immortalized -VS- keratinocytes empty vector (GSE50568/GPL570) | −0.13 | 0.000 | −0.24 | 0.000 |
| vitro131 | reconstituted epidermis scabies mite extract -VS -reconstituted epidermis untreated (GSE48459/GPL6244) | −0.072 | 0.004 | −0.22 | 0.000 |
| vitro132 | HaCaT keratinocytes cidofovir -VS- HaCaT keratinocytes untreated (GSE39293/GPL570) | 0.206 | 0.000 | 0.251 | 0.000 |
| vitro145 | HaCaT keratinocytes cobalt(II) chloride 3 hrs -VS- HaCaT keratinocytes water control (GSE16727/GPL4133) | −0.166 | 0.000 | −0.15 | 0.002 |
| vitro153 | reconstituted epidermis 24 hrs after 10 cGy radiation -VS- reconstituted epidermis control (GSE29344/GPL6883) | −0.078 | 0.003 | −0.08 | 0.126 |
| vitro159 | keratinocytes poly(I:C) 24 hrs -VS- keratinocytes untreated (GSE21260/GPL6104) | 0.069 | 0.008 | 0.249 | 0.000 |
| vitro164 | HaCaT keratinocytes IL1A + IL17 + IL22 + TNF + OsM -VS- HaCaT keratinocytes untreated (GSE37361/GPL13607) | 0.102 | 0.000 | 0.196 | 0.000 |
| vitro2 | reconstituted epidermis IL1a -VS- reconstituted epidermis untreated (GSE25400/GPL6244) | 0.104 | 0.000 | 0.163 | 0.001 |
| vitro20 | keratinocytes IL26d -VS- keratinocytes untreated (GSE7216/GPL570) | 0.052 | 0.040 | 0.077 | 0.126 |
| vitro21 | keratinocytes IFNa -VS- keratinocytes untreated (GSE36287/GPL570) | 0.089 | 0.000 | 0.105 | 0.032 |
| vitro22 | DK7 keratinocytes IFNg -VS- DK7 keratinocytes untreated (GSE1132/GPL97) | 0.13 | 0.000 | 0.138 | 0.004 |
| vitro24 | keratinocytes IFNg -VS- keratinocytes untreated (GSE7216/GPL570) | 0.086 | 0.001 | 0.306 | 0.000 |
| vitro26 | keratinocytes IFNg -VS- keratinocytes untreated (GSE36287/GPL570) | 0.053 | 0.034 | 0.104 | 0.034 |

TABLE 2-continued

Table 2. Skin - relevant gene expression comparisons from Gene Expression Omnibus (GEO), matched (significantly correlated or significantly inversely correlated) with genes down-regulated by both - retinoic acid AND SBD.SE. (GSE: GEO Series; GPL: GEO Platforms; stats between −0.05 and 0.05 considered not significant match).

| Experiment | GOE Series (GSE)/GEO Platform (GPL) | ATRA | | SBD.SE | |
|---|---|---|---|---|---|
| ID | Label | Stat | FDR | Stat | FDR |
| vitro31 | keratinocytes EGF 100% confluence- VS-keratinocytes untreated 100% confluence (GSE32217/GPL6244) | 0.155 | 0.000 | 0.211 | 0.000 |
| vitro35 | keratinocytes TGFalpha 120 min -VS- keratinocytes untreated (GSE8531/GPL571) | 0.127 | 0.000 | 0.133 | 0.016 |
| vitro41 | HaCaT keratinocytes TNF -VS- HaCaT keratinocytes untreated (GSE32975/GPL570) | 0.141 | 0.000 | 0.112 | 0.022 |
| vitro45 | keratinocytes TNF -VS- keratinocytes untreated (GSE36387/GPL10558) | 0.049 | 0.057 | 0.132 | 0.006 |
| vitro47 | keratinocytes IL4 + IL13 DUOX1 siRNA -VS- keratinocytes untreated (GSE20706/GPL6480) | −0.081 | 0.001 | −0.3 | 0.000 |
| vitro5 | reconstituted epidermis IL1F6 -VS- reconstituted epidermis untreated (GSE25400/GPL6244) | 0.09 | 0.000 | 0.118 | 0.017 |
| vitro50 | HaCaT keratinocytes TNF + IFNg -VS- HaCaT keratinocytes untreated (GSE20297/GPL570) | 0.174 | 0.000 | 0.295 | 0.000 |
| vitro51 | HaCaT keratinocytes TNF + IFNg + terbutaline -VS- HaCaT keratinocytes untreated (GSE20297/GPL570) | 0.156 | 0.000 | 0.337 | 0.000 |
| vitro52 | HaCaT keratinocytes TNF + IFNg + GW9508 -VS- HaCaT keratinocytes untreated (GSE20297/GPL570) | 0.149 | 0.000 | 0.258 | 0.000 |
| vitro53 | keratinocytes *staphylococcus aureus* 24 hrs- VS-keratinocytes untreated (GSE24370/GPL4133) | −0.112 | 0.000 | −0.19 | 0.000 |
| vitro56 | keratinocytes cis urocanic acid -VS- keratinocytes untreated (GSE8760/GPL96) | 0.09 | 0.001 | −0.13 | 0.017 |
| vitro57 | keratinocytes trans urocanic acid -VS- keratinocytes untreated (GSE8760/GPL96) | 0.058 | 0.041 | 0.118 | 0.032 |
| vitro6 | reconstituted epidermis IL1F8 -VS- reconstituted epidermis untreated (GSE25400/GPL6244) | 0.114 | 0.000 | 0.171 | 0.000 |
| vitro64 | keratinocytes dexamethasone 24 hr- VS-keratinocytes untreated (GSE26487/GPL8300) | −0.068 | 0.035 | −0.12 | 0.039 |
| vitro65 | keratinocytes dexamethasone 48 hr- VS-keratinocytes untreated (GSE26487/GPL8300) | −0.069 | 0.034 | −0.13 | 0.028 |
| vitro66 | keratinocytes dexamethasone 72 hr- VS-keratinocyte untreated (GSE26487/GPL8300) | −0.068 | 0.035 | −0.17 | 0.002 |
| vitro67 | keratinocytes calcium 1 hr -VS- keratinocytes untreated (GSE38628/GPL6244) | 0.084 | 0.001 | 0.082 | 0.103 |
| vitro7 | reconstituted epidermis IL1F9 -VS- reconstituted epidermis untreated (GSE25400/GPL6244) | 0.106 | 0.000 | 0.176 | 0.000 |
| vitro73 | keratinocytes differentiating day 7 with CA -VS- keratinocytes proliferating day 0 (GSE21413/GPL571) | −0.118 | 0.000 | −0.17 | 0.002 |
| vitro79 | keratinocytes EPHB2 treated -VS- keratinocytes untreated (GSE26523/GPL571) | −0.072 | 0.010 | −0.22 | 0.000 |
| vitro8 | keratinocytes IL4 -VS- keratinocytes untreated (GSE36287/GPL570) | −0.117 | 0.000 | −0.19 | 0.000 |
| vitro97 | HaCaT keratinocytes MYC siRNA- VS-HaCaT keratinocytes control siRNA (GSE17394/GPL4803) | 0.101 | 0.001 | 0.148 | 0.010 |
| vivo11 | PN skin -VS- NN skin (GSE14905/GPL570) | −0.053 | 0.035 | −0.13 | 0.011 |
| vivo110 | reticular dermis -VS- NN Skin (GSE42114/GPL570) | 0.059 | 0.017 | 0.121 | 0.014 |
| vivo111 | wound day 14 -VS- baseline (GSE50425/GPL10558) | 0.087 | 0.001 | 0.146 | 0.002 |

TABLE 2-continued

Table 2. Skin - relevant gene expression comparisons from Gene Expression Omnibus (GEO), matched (significantly correlated or significantly inversely correlated) with genes down-regulated by both - retinoic acid AND SBD.SE. (GSE: GEO Series; GPL: GEO Platforms; stats between −0.05 and 0.05 considered not significant match).

| Experiment ID | GOE Series (GSE)/GEO Platform (GPL) Label | ATRA Stat | ATRA FDR | SBD.SE Stat | SBD.SE FDR |
|---|---|---|---|---|---|
| vivo112 | wound day 21 -VS- baseline (GSE50425/GPL10558) | 0.079 | 0.002 | 0.101 | 0.038 |
| vivo114 | dermatomyositis -VS- NN Skin (GSE46239/GPL570) | 0.109 | 0.000 | 0.129 | 0.008 |
| vivo118 | narrow-band UVB 24 hrs -VS- uninvolved skin (GSE41078/GPL571) | 0.082 | 0.004 | 0.13 | 0.018 |
| vivo12 | PP epidermis -VS- PN epidermis (GSE26866/GPL571) | 0.066 | 0.018 | 0.207 | 0.000 |
| vivo13 | PP dermis -VS- PN dermis (GSE26866/GPL571) | 0.074 | 0.008 | 0.16 | 0.003 |
| vivo15 | PP skin 1 wk etanercept -VS- PN skin baseline (GSE11903/GPL571) | 0.074 | 0.008 | 0.179 | 0.001 |
| vivo17 | PP skin 4 wk etanercept -VS- PN skin baseline (GSE11903/GPL571) | 0.061 | 0.032 | 0.166 | 0.002 |
| vivo18 | PP skin 12 wk etanercept -VS- PN skin baseline (GSE11903/GPL571) | 0.056 | 0.047 | 0.091 | 0.103 |
| vivo2 | PP skin -VS- PN skin (GSE6710/GPL96) | 0.055 | 0.052 | 0.143 | 0.009 |
| vivo22 | PP skin etanercept 12 wk -VS- PP skin baseline (GSE11903/GPL571) | −0.077 | 0.006 | −0.18 | 0.001 |
| vivo23 | PP skin LY2439821 2 wk -VS- PP skin baseline (GSE31652/GPL571) | −0.105 | 0.000 | −0.2 | 0.000 |
| vivo24 | PP skin LY2439821 2 wk -VS- PP skin placebo 2 wk (GSE31652/GPL571) | −0.077 | 0.006 | −0.22 | 0.000 |
| vivo25 | PN skin IFNg-treated 24 hrs -VS- PN skin baseline (GSE32407/GPL571) | 0.084 | 0.003 | 0.158 | 0.003 |
| vivo26 | PN skin IFNg-treated 24 hrs -VS- PN skin placebo 24 hrs (GSE32407/GPL571) | 0.076 | 0.007 | 0.158 | 0.003 |
| vivo27 | NN skin IFNg-treated 24 hrs -VS- NN skin baseline (GSE32407/GPL571) | 0.073 | 0.009 | 0.111 | 0.045 |
| vivo29 | PP skin efalizumab 12 wk -VS- PP skin baseline (GSE30768/GPL571) | −0.053 | 0.060 | −0.2 | 0.000 |
| vivo3 | PP skin -VS- PN skin (GSE11903/GPL571) | 0.06 | 0.033 | 0.183 | 0.001 |
| vivo30 | PP skin post-efalizumah relapse -VS- PP skin efalizumab 12 wk (GSE30768/GPL571) | 0.053 | 0.059 | 0.166 | 0.002 |
| vivo42 | atopic dermatitis lesion -VS- NN skin (GSE5667/GPL96 + GPL97) | 0.093 | 0.000 | 0.095 | 0.055 |
| vivo47 | epidermis sodium lauryl sulphate 4 hrs- VS-epidermis basline (GSE18206/GPL570) | 0.144 | 0.000 | 0.106 | 0.031 |
| vivo48 | epidermis sodium lauryl sulphate 24 hrs- VS-epidermis basline (GSE18206/GPL570) | 0.063 | 0.012 | 0.157 | 0.001 |
| vivo52 | epidermis nonanoic acid 24 hrs -VS- epidermis basline (GSE18206/GPL570) | 0.086 | 0.001 | 0.102 | 0.037 |
| vivo61 | wound 3 days healed -VS- uninvolved skin (GSE28914/GPL570) | 0.063 | 0.012 | 0.16 | 0.001 |
| vivo7 | PP skin -VS- PN skin (GSE30999/GPL570) | 0.06 | 0.016 | 0.114 | 0.021 |
| vivo73 | skin diffuse cutaneous systemic sclerosis -VS- NN skin (GSE32413/GPL4133) | −0.093 | 0.000 | −0.11 | 0.024 |
| vivo78 | atopic eczema -VS- NN skin (GSE6012/GPL96) | 0.064 | 0.023 | 0.103 | 0.061 |
| vivo80 | epidermis epidermolysis bullosa simplex -VS- normal epidermis (GSE28315/GPL6244) | 0.05 | 0.051 | 0.172 | 0.000 |
| vivo82 | skin *Haemophilus ducreyi* infected- VS-skin PBS treated (GSE5547/GPL570) | 0.07 | 0.005 | 0.15 | 0.002 |
| vivo89 | benign nevi -VS- NN skin (GSE4587/GPL570) | −0.065 | 0.009 | −0.06 | 0.227 |
| vivo97 | basal cell carcinoma morphoeic -VS- NN skin (GSE6520/GPL3877) | 0.059 | 0.031 | −0.09 | 0.088 |

Table 3 shows relevant gene expression comparisons from Gene Expression Omnibus (GEO), matched (significantly correlated or significantly inversely correlated) with genes down-regulated by both—retinol palmitate and SBD.SE. (GSE: GEO Series; GPL: GEO Platforms; stats between −0.05 and 0.05 considered not significant match).

TABLE 3

| ID | Label | SBD.SE Stat | SBD.SE FDR | Retinol-palmitate Stat | Retinol-palmitate FDR |
|---|---|---|---|---|---|
| esnp31 | rs2431697 (PTTG1/5) | −0.135 | 4.59E−05 | −0.059 | 0.1104 |
| esnp43 | rs842636 (REL/2) | 0.08 | 0.018248 | 0.077 | 0.0372 |
| esnp44 | rs13017599 (REL/2) | 0.079 | 0.020038 | 0.111 | 0.0018 |
| esnp9 | rs20541 (IL13/IL4/5) | −0.106 | 0.001478 | −0.052 | 0.1736 |
| vitro106 | HaCaT keratinocytes ZNF750 RNAi -VS- HaCaT keratinocytes control (GSE38039/GPL6244) | 0.189 | 1.19E−08 | 0.13 | 0.0003 |
| vitro129 | keratinocytes N/Tert immortalized -VS- keratinocytes empty vector (GSE50568/GPL570) | 0.105 | 0.001487 | 0.085 | 0.0201 |
| vitro131 | reconstituted epidermis scabies mite extract -VS- reconstituted epidermis untreated (GSE48459/GPL6244) | −0.105 | 0.001748 | −0.092 | 0.0139 |
| vitro132 | HaCaT keratinocytes cidofovir -VS- HaCaT keratinocytes untreated (GSE39293/GPL570) | −0.116 | 0.000438 | −0.065 | 0.0792 |
| vitro134 | keratinocytes keloid -VS- keratinocytes uninvolved (GSE44270/GPL6244) | 0.153 | 4.39E−06 | 0.052 | 0.1870 |
| vitro137 | N/TERT-1 keratinocytes miR-198 -VS- N/TERT-1 keratinocytes control (GSE37967/GPL10558) | 0.197 | 7.41E−09 | 0.098 | 0.0079 |
| vitro139 | HaCaT keratinocytes miR-483-3p overexpression -VS- HaCaT keratinocytes control (GSE19931/GPL1456) | −0.08 | 0.042716 | −0.073 | 0.1133 |
| vitro145 | HaCaT keratinocytes cobalt(II) chloride 3 hrs -VS- HaCaT keratinocytes water control (GSE16727/GPL4133) | 0.1 | 0.003416 | 0.095 | 0.0139 |
| vitro148 | HaCaT keratinocytes cobalt(II) chloride 3 hrs -VS- HaCaT keratinocytes water control (GSE16727/GPL4133) | 0.122 | 0.000356 | 0.065 | 0.0961 |
| vitro15 | keratinocytes IL19 -VS- keratinocytes untreated (GSE7216/GPL570) | −0.124 | 0.000184 | −0.099 | 0.0060 |
| vitro150 | reconstituted epidermis 0 hrs after 10 cGy radiation -VS- reconstituted epidermis control (GSE29344/GPL6883) | −0.073 | 0.037531 | −0.119 | 0.0010 |
| vitro151 | reconstituted epidermis 3 hrs after 10 cGy radiation -VS- reconstituted epidermis control (GSE29344/GPL6883) | −0.088 | 0.011816 | −0.071 | 0.0607 |
| vitro152 | reconstituted epidermis 8 hrs after 10 cGy radiation -VS- reconstituted epidermis control (GSE29344/GPL6883) | −0.078 | 0.026866 | −0.051 | 0.1926 |
| vitro153 | reconstituted epidermis 24 hrs after 10 cGy radiation -VS- reconstituted epidermis control (GSE29344/GPL6883) | −0.154 | 5.32E−06 | −0.156 | 0.0000 |
| vitro156 | reconstituted epidermis 8 hrs after 100 cGy radiation -VS- reconstituted epidermis control (GSE29344/GPL6883) | −0.119 | 0.000455 | −0.129 | 0.0003 |
| vitro157 | reconstituted epidermis 24 hrs after 100 cGy radiation -VS- reconstituted epidermis control (GSE29344/GPL6883) | −0.173 | 3.33E−07 | −0.136 | 0.0002 |
| vitro16 | keratinocytes IL20 -VS- keratinocytes untreated (GSE7216/GPL570) | −0.088 | 0.008914 | −0.116 | 0.0010 |
| vitro165 | HaCaT keratinocytes Ino-C2-PAF + IL1A + IL17 + IL22 + TNF + OsM -VS- HaCaT keratinocytes untreated (GSE37361/GPL13607) | −0.119 | 0.000438 | −0.151 | 0.0000 |
| vitro23 | keratinocytes IFNg -VS- keratinocytes untreated (GSE440/GPL8300) | −0.111 | 0.007064 | −0.09 | 0.0658 |
| vitro24 | keratinocytes IFNg -VS- keratinocytes untreated (GSE7216/GPL570) | 0.096 | 0.003841 | 0.09 | 0.0139 |
| vitro27 | HaCaT keratinocytes EGF -VS- HaCaT keratinocytes untreated (GSE32975/GPL570) | −0.153 | 3.64E−06 | −0.137 | 0.0001 |
| vitro31 | keratinocytes EGF 100% confluence -VS- keratinocytes untreated 100% confluence (GSE32217/GPL6244) | 0.145 | 1.5E−05 | 0.119 | 0.0010 |
| vitro4 | reconstituted epidermis IL1F5 -VS- reconstituted epidermis untreated (GSE25400/GPL6244) | 0.071 | 0.040505 | 0.132 | 0.0002 |

TABLE 3-continued

| ID | Label | SBD.SE Stat | SBD.SE FDR | Retinol-palmitate Stat | Retinol-palmitate FDR |
|---|---|---|---|---|---|
| vitro41 | HaCaT keratinocytes TNF -VS- HaCaT keratinocytes untreated (GSE32975/GPL570) | −0.089 | 0.007716 | −0.062 | 0.0961 |
| vitro50 | HaCaT keratinocytes TNF + IFNg -VS- HaCaT keratinocytes untreated (GSE20297/GPL570) | −0.132 | 6.39E−05 | −0.087 | 0.0182 |
| vitro51 | HaCaT keratinocytes TNF + IFNg + terbutaline -VS- HaCaT keratinocytes untreated (GSE20297/GPL570) | −0.104 | 0.001602 | −0.081 | 0.0269 |
| vitro52 | HaCaT keratinocytes TNF + IFNg + GW9508 -VS- HaCaT keratinocytes untreated (GSE20297/GPL570) | −0.137 | 3.22E−05 | −0.087 | 0.0176 |
| vitro53 | keratinocytes *staphylococcus aureus* 24 hrs- VS-keratinocytes untreated (GSE24370/GPL4133) | −0.132 | 0.000108 | −0.089 | 0.0201 |
| vitro56 | keratinocytes cis urocanic acid -VS- keratinocytes untreated (GSE8760/GPL96) | −0.173 | 1.3E−06 | −0.22 | 0.0000 |
| vitro59 | keratinocytes solar ultraviolet radiation- VS-keratinocytes untreated (GSE8760/GPL96) | −0.113 | 0.001602 | −0.118 | 0.0028 |
| vitro6 | reconstituted epidermis ILIF8 -VS- reconstituted epidermis untreated (GSE25400/GPL6244) | 0.12 | 0.000356 | 0.063 | 0.0961 |
| vitro61 | reconstituted epidermis 16 hr radiation- VS-reconstituted epidermis untreated (GSE23901/GPL4133) | −0.079 | 0.025383 | −0.156 | 0.0000 |
| vitro86 | keratinocytes EXOSC9 GRHL3 siRNA- VS-keratinocytes untreated (GSE37637/GPL570) | −0.134 | 4.59E−05 | −0.129 | 0.0002 |
| vitro87 | keratinocytes GRHL3 siRNA -VS- keratinocytes untreated (GSE37049/GPL6244) | 0.106 | 0.001487 | 0.063 | 0.0975 |
| vitro88 | keratinocytes KLF4 siRNA -VS- keratinocytes untreated (GSE32685/GPL570) | 0.175 | 1.25E−07 | 0.109 | 0.0019 |
| vitro89 | keratinocytes MLL2 siRNA -VS- keratinocytes scrambled siRNA (GSE37570/GPL6244) | 0.151 | 5.45E−06 | 0.131 | 0.0002 |
| vitro9 | keratinocytes IL13 -VS- keratinocytes untreated (GSE36287/GPL570) | 0.091 | 0.006886 | 0.077 | 0.0380 |
| vivo114 | dermatomyositis -VS- NN Skin (GSE46239/GPL570) | 0.116 | 0.000436 | 0.072 | 0.0512 |
| vivo118 | narrow-band UVB 24 hrs -VS- uninvolved skin (GSE41078/GPL571) | −0.116 | 0.001201 | −0.117 | 0.0030 |
| vivo25 | PN skin IFNg-treated 24 hrs -VS- PN skin baseline (GSE32407/GPL571) | −0.11 | 0.001995 | −0.062 | 0.1403 |
| vivo26 | PN skin IFNg-treated 24 hrs -VS- PN skin placebo 24 hrs (GSE32407/GPL571) | −0.119 | 0.000849 | −0.074 | 0.0738 |
| vivo27 | NN skin IFNg-treated 24 hrs -VS- NN skin baseline (GSE32407/GPL571) | −0.09 | 0.013243 | −0.065 | 0.1158 |
| vivo32 | atopic dermatitis uninvolved epidermis- VS-NN epidermis (GSE26952/GPL2700) | 0.098 | 0.00404 | 0.069 | 0.0879 |
| vivo42 | atopic dermatitis lesion -VS- NN skin (GSE5667/GPL96 + GPL97) | 0.11 | 0.000924 | 0.085 | 0.0214 |
| vivo43 | atopic dermatitis lesion -VS- uninvolved skin (GSE5667/GPL96 + GPL97) | 0.111 | 0.000839 | 0.089 | 0.0164 |
| vivo49 | epidermis sodium lauryl sulphate 11 days- VS-epidermis basline (GSE18206/GPL570) | 0.152 | 4.05E−06 | 0.118 | 0.0008 |
| vivo50 | epidermis nonanoic acid 30 min -VS- epidermis basline (GSE18206/GPL570) | 0.125 | 0.000157 | 0.15 | 0.0000 |
| vivo51 | epidermis nonanoic acid 4 hrs -VS- epidermis basline (GSE18206/GPL570) | 0.103 | 0.001804 | 0.057 | 0.1287 |
| vivo53 | epidermis nonanoic acid 11 days -VS- epidermis basline (GSE18206/GPL570) | 0.17 | 2.89E−07 | 0.12 | 0.0006 |
| vivo82 | skin *Haemophilus ducreyi* infected -VS- skin PBS treated (GSE5547/GPL570) | −0.105 | 0.001548 | −0.104 | 0.0034 |

Table 4 shows relevant gene expression comparisons from Gene Expression Omnibus (GEO), matched (significantly correlated or significantly inversely correlated) with genes down-regulated by SBD.SE, but not matching with retinol palmitate—down-regulated genes. (GSE: GEO Series; GPL: GEO Platforms; stats between −0.05 and 0.05 considered not a significant match). Underlined are the comparisons, which match retinol palmitate AND SBD.SE but with opposite stats directionality.

TABLE 4

| ID | Label | Stat | FDR |
|---|---|---|---|
| esnp13 | rs2066808 (IL23A/12) | −0.083 | 0.014559 |
| esnp14 | rs2066807 (IL23A/12) | −0.089 | 0.00791 |
| esnp17 | rs11209026 (IL23R/1) | 0.093 | 0.0056 |
| esnp2 | rs12191877 (HLA-C/6) | 0.102 | 0.001971 |
| esnp21 | rs12586317 (NFKBIA/14) | −0.076 | 0.025383 |
| esnp22 | rs696 (NFKBIA/14) | 0.101 | 0.002198 |
| esnp23 | rs1008953 (SDC4/20) | −0.129 | 0.000103 |
| esnp3 | rs2082412 (IL12B/5) | 0.112 | 0.000641 |
| esnp35 | rs3751385 (GJB2/13) | −0.081 | 0.016594 |
| esnp37 | rs11084211 (ZNF816A/19) | 0.072 | 0.035724 |
| esnp38 | rs13210247 (TRAF3IP2/6) | 0.096 | 0.003841 |
| esnp4 | rs3212227 (IL12B/5) | 0.084 | 0.013075 |
| esnp40 | Deletion (LCE3/1) | 0.072 | 0.034661 |
| esnp41 | rs6702463 (LCE3/1) | 0.102 | 0.00197 |
| esnp42 | rs4112788 (LCE3/1) | 0.071 | 0.038579 |
| mouse11 | K5-Tie2 psoriasiform lesion -VS- normal control skin (GSE27628/GSE1261) | 0.077 | 0.040573 |
| mouse3 | MEF wild type IL17 + TNF -VS- MEF wild type mock (GSE24873/GPL1261) | −0.115 | 0.001607 |
| vitro112 | keratinocytes phevalin -VS- keratinocytes untreated (GSE32920/GPL571) | 0.097 | 0.007555 |
| vitro121 | keratinocytes NFX1-123 overexpression -VS- keratinocytes control (GSE43082/GPL10558) | 0.07 | 0.040573 |
| vitro122 | keratinocytes PD98059 24/48 HRS -VS- keratinocytes untreated (GSE50591/GPL571) | −0.082 | 0.026454 |
| vitro124 | keratinocytes SP60125 SB203580 PD98059 24/48 HRS -VS- keratinocytes untreated (GSE50591/GPL571) | −0.116 | 0.001152 |
| vitro128 | keratinocytes mitomycin C 18 hrs -VS- keratincytes untreated (GSE50568/GPL570) | −0.147 | 7.57E−06 |
| vitro147 | HaCaT keratinocytes tungsten carbide cobalt 3 days -VS- HaCaT keratinocytes water control (GSE16727/GPL4133) | 0.09 | 0.009315 |
| vitro160 | HaCaT keratinocytes 5'-aza-2-deoxycytidine -VS- HaCaT keratinocytes untreated (GSE33493/GPL6883) | −0.098 | 0.00415 |
| vitro2 | reconstituted epidermis IL1a -VS- reconstituted epidermis untreated (GSE25400/GPL6244) | 0.123 | 0.00023 |
| vitro46 | keratinocytes IL4 + IL13 -VS- keratinocytes untreated (GSE20706/GPL6480) | 0.073 | 0.037817 |
| vitro48 | keratinocytes IL17 + TNF 1 ng/mL -VS- keratinocytes untreated (GSE24767/GPL6947) | −0.074 | 0.030808 |
| vitro94 | HaCaT keratinocytes GLI1 overexpression 72 hrs- VS-HaCaT keratinocytes untreated (GSE1434/GPL1260) | 0.106 | 0.017809 |
| vitro97 | HaCaT keratinocytes MYC siRNA -VS- HaCaT keratinocytes control siRNA (GSE17394/GPL4803) | −0.099 | 0.013659 |
| vivo1 | PP skin -VS- PN skin (GSE2737/GPL91) | 0.085 | 0.041638 |
| vivo110 | reticular dermis -VS- NN Skin (GSE42114/GPL570) | −0.074 | 0.030678 |
| vitro71 | keratinocytes calcium 24 hr -VS- keratinocytes untreated (GSE38628/GPL6244) | 0.11 | 0.001058 |
| vitro84 | keratinocytes ERK1 ERK2 siRNA -VS- keratinocytes scrambled siRNA (GSE15417/GPL571) | −0.152 | 1.94E−05 |
| vivo115 | seborrheic keratosis -VS- uninvolved Skin (GSE22998/(GPL570) | 0.075 | 0.027801 |
| vivo116 | eschars in mediterranean spotted fever -VS- NN Skin (GSE32993/GPL6480) | 0.097 | 0.004271 |
| vivo12 | PP epidermis -VS- PN epidermis (GSE26866/GPL571) | 0.084 | 0.022616 |
| vivo120 | atopic dermatitis chronic -VS- uninvolved skin (GSE36842/GPL570) | 0.125 | 0.000157 |
| vivo15 | PP skin 1 wk etanercept -VS- PN skin baseline (GSE11903/GPL571) | 0.108 | 0.002525 |
| vivo19 | PP skin etanercept 1 wk -VS- PP skin baseline (GSE11903/GPL571) | −0.134 | 0.000176 |
| vivo2 | PP skin -VS- PN skin (GSE6710/GPL96) | 0.151 | 2.19E−05 |
| vivo20 | PP skin etanexcept 2 wk -VS- PP skin baseline (GSE11903/GPL571) | −0.166 | 3.64E−06 |
| vivo21 | PP skin etanercept 4 wk -VS- PP skin baseline (GSE11903/GPL571) | −0.137 | 0.000138 |
| vivo22 | PP skin etanercept 12 wk -VS- PP skin baseline (GSE11903/GPL571) | −0.15 | 2.32E−05 |
| vivo23 | PP skin LY2439821 2 wk -VS- PP skin baseline (GSE31652/GPL571) | −0.172 | 1.47E−06 |

TABLE 4-continued

| ID | Label | Stat | FDR |
|---|---|---|---|
| vivo24 | PP skin LY2439821 2 wk -VS- PP skin placebo 2 wk (GSE31652/GPL571) | −0.163 | 4.39E−06 |
| vivo29 | PP skin efalizumab 12 wk -VS- PP skin baseline (GSE30768/GPL571) | −0.181 | 3.33E−07 |
| vivo3 | PP skin -VS- PN skin (GSE11903/GPL571) | 0.126 | 0.000436 |
| vivo30 | PP skin post-efalizumab relapse -VS- PP skin efalizumab 12 wk (GSE30768/GPL571) | 0.151 | 2.16E−05 |
| vivo33 | atopic dermatitis lesion -VS- atopic dermatitis uninvolved skin (GSE27887/GPL570) | 0.07 | 0.040505 |
| vivo34 | atopic dermatitis NB-UVB-treated lesion -VS- atopic dermatitis NB-UVB-treated uninvolved skin (GSE27887/GPL570) | 0.103 | 0.001748 |
| vivo37 | atopic dermatitis lesion betamethasone -VS- atopic dermatitis lesion baseline (GSE32473/GPL570) | −0.085 | 0.011982 |
| vivo39 | atopic dermatitis lesion -VS- atopic dermatitis uninvolved skin (GSE32924/GPL570) | 0.124 | 0.000176 |
| vivo4 | PP skin -VS- PN skin (GSE13355/GPL570) | 0.113 | 0.000595 |
| vivo5 | PP skin -VS- PN skin (GSE14905/GPL570) | 0.093 | 0.005425 |
| vivo52 | epidermis nonanoic acid 24 hrs -VS- epidermis basline (GSE18206/GPL570) | 0.084 | 0.013458 |
| vivo59 | wound margin 7+ days healed -VS- NN skin (GSE8056/GPL570) | 0.094 | 0.004727 |
| vivo6 | PP skin -VS- PN skin (GSE26866/GPL571) | 0.127 | 0.000392 |
| vivo7 | PP skin -VS- PN skin (GSE30999/GPL570) | 0.115 | 0.000482 |
| vivo73 | skin diffuse cutaneous systemic sclerosis -VS- NN skin (GSE32413/GPL4133) | 0.088 | 0.012028 |
| vivo76 | skin isotretinoin 8 wks -VS- skin baseline (GSE11792/GPL571) | −0.128 | 0.000356 |
| vivo8 | PP skin -VS- NN skin (GSE13355/GPL570) | 0.123 | 0.000192 |
| vivo83 | basal cell carcinoma -VS- NN skin (GSE7553/GPL570) | 0.081 | 0.017196 |
| vivo85 | squamous cell carcinoma -VS- NN skin (GSE7553/GPL570) | 0.12 | 0.000312 |
| vivo88 | squamous cell carcinoma -VS- NN skin (GSE2503/GPL96) | 0.111 | 0.001804 |
| vivo9 | PP skin -VS- NN skin (GSE14905/GPL570) | 0.132 | 6.8E−05 |
| vivo93 | melanoma in situ -VS- NN skin (GSE4587/GPL570) | 0.102 | 0.001971 |

Table 5 shows a selection of gene expression comparisons from Gene Expression Omnibus (GEO) inversely correlated with SBD.SE effect in UVA-irradiated skin substitutes (GSE: GEO Series; GPL: GEO Platforms).

TABLE 5

| ID | Label | Stat | P value |
|---|---|---|---|
| vivo101 | UVA radiation 0.1 minimal erythema dose- VS-untreated skin (GSE22083/GPL96) | −0.096 | 0.005 |
| vivo99 | UVB radiation 1 minimal erythema dose- VS-untreated skin (GSE22083/GPL96) | −0.088 | 0.011 |
| vivo100 | UVB radiation 100 J/m2 -VS- untreated skin (GSE22083/GPL96) | −0.102 | 0.003 |

Table 6 shows antioxidant activity of SBD.SE, SBD.FA and bakuchiol expressed as % of coloration in water control measured at 520 nm, which is proportional to the non-reacted DPPH.

TABLE 6

| Test Material | Dose (ug/ml) | DPPH color (% Control) | p value |
|---|---|---|---|
| H2O | 0 | 100 | 1 |
| bakuchiol | 10 | 46 | 0.001 |
| bakuchiol | 2 | 92 | 0.379 |
| bakuchiol | 0.5 | 85 | 0.154 |
| SBD.FA | 10 | 60 | 0.004 |
| SBD.FA | 2 | 99 | 0.708 |
| SBD.FA | 0.5 | 102 | 0.810 |
| SBD.SE | 40 | 6 | 0.000 |
| SBD.SE | 16 | 28 | 0.000 |

TABLE 6-continued

| Test Material | Dose (ug/ml) | DPPH color (% Control) | p value |
|---|---|---|---|
| SBD.SE | 10 | 59 | 0.003 |
| SBD.SE | 2 | 89 | 0.189 |
| SBD.SE | 0.5 | 86 | 0.164 |

Example 4: Resistance to Decomposition by UVB Irradiation

Figure 3:
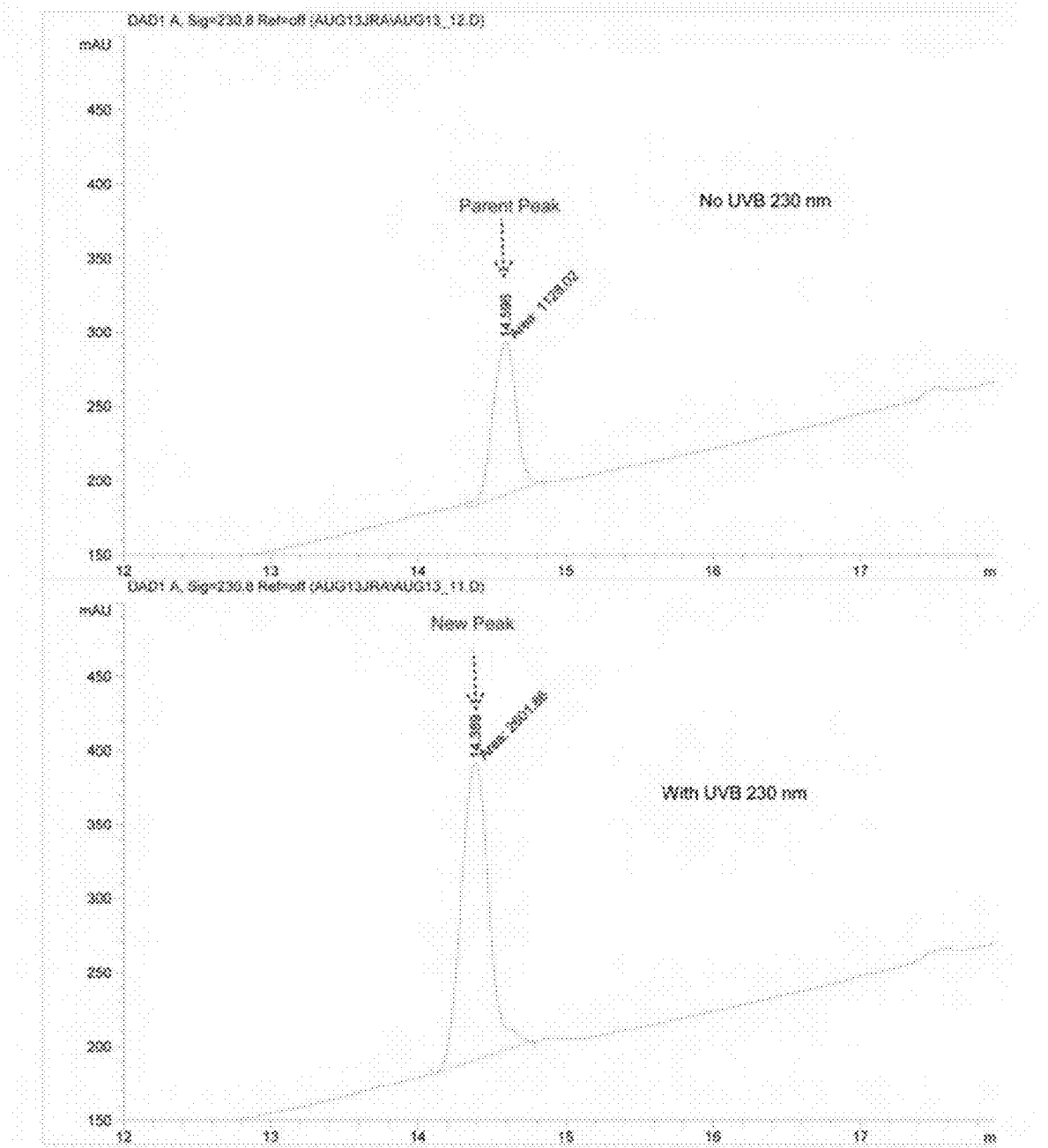
FIG. 3: HPLC chromatogram of non-irradiated and UVB-irradiated bakuchiol, detected at 230 nm.
Figure 7:
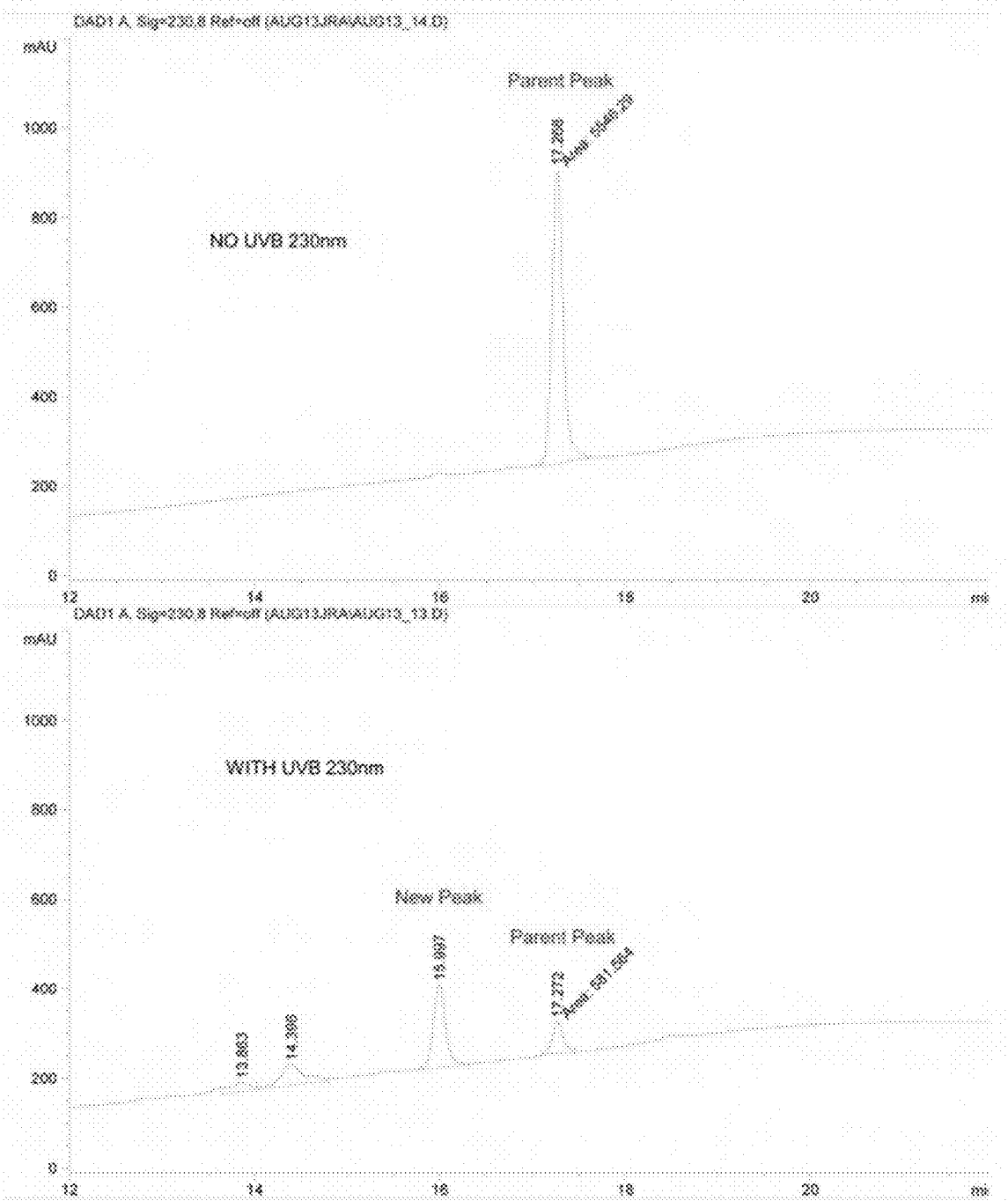
FIG. 7: HPLC chromatogram of non-irradiated and UVB-irradiated SBD.SE, detected at 230 nm.
Figure 8:
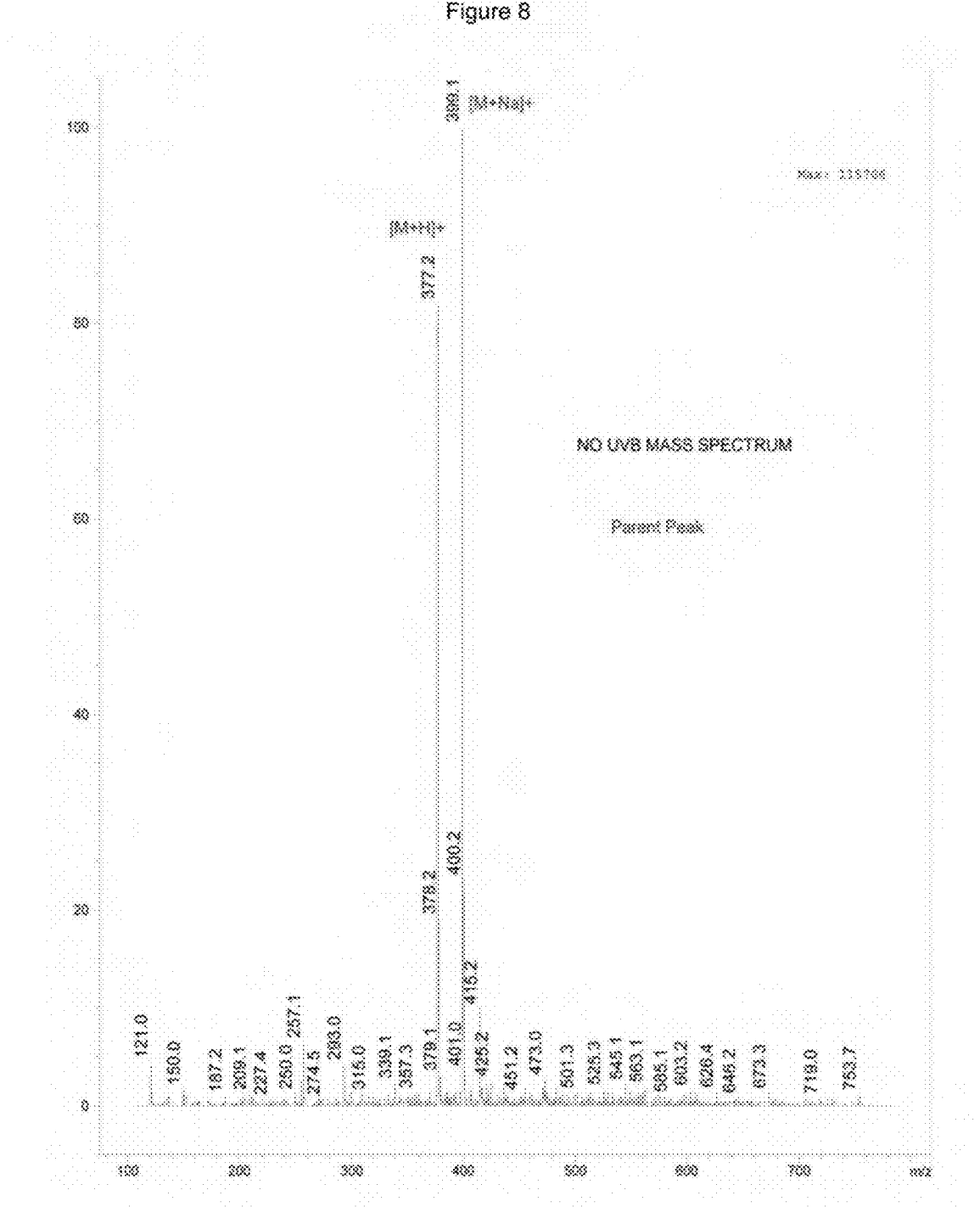
FIG. 8: Mass spectrum of non-irradiated SBD.SE.
Figure 9:
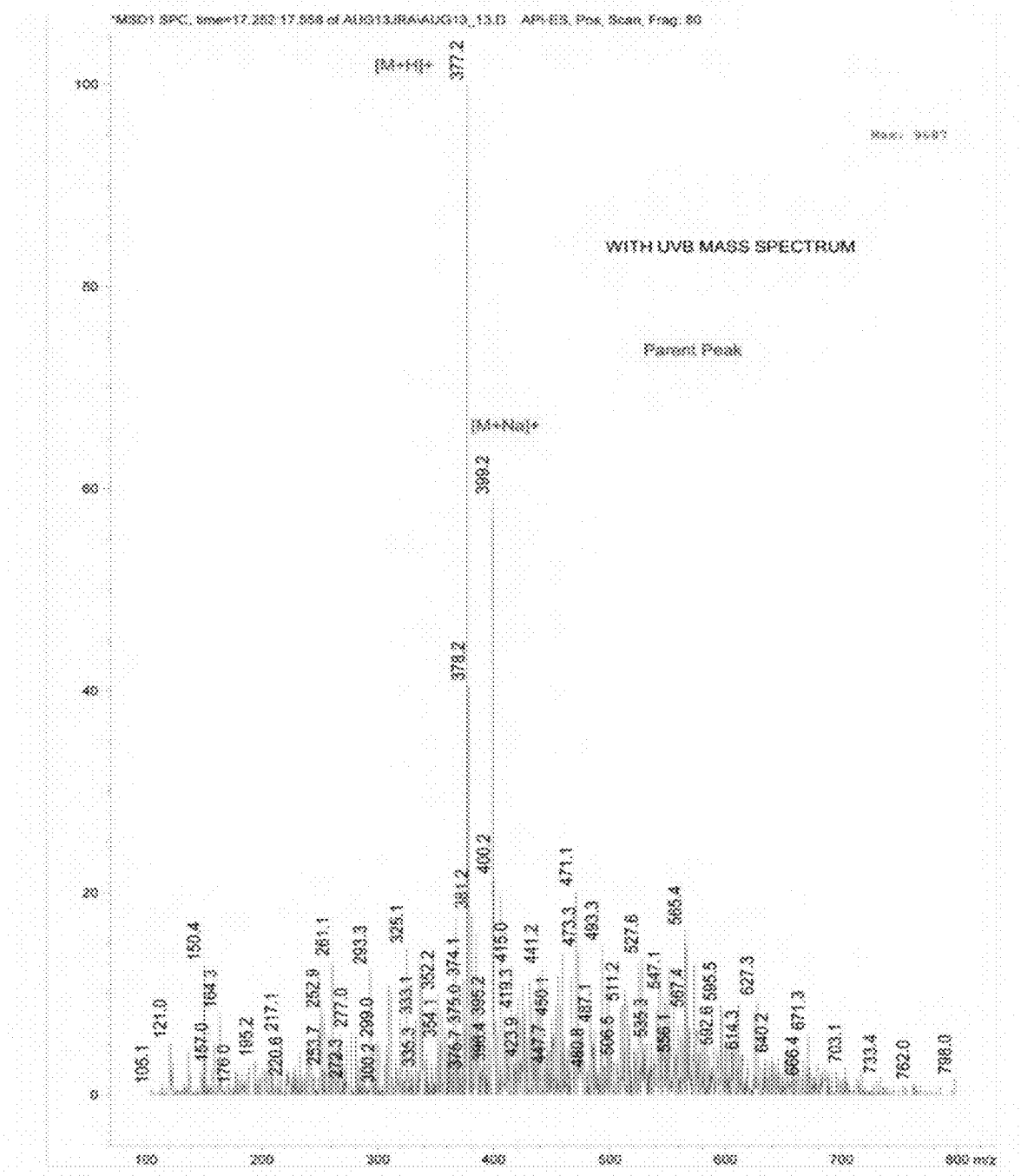
FIG. 9: Mass spectrum of UVB-irradiated SBD.SE.

This example demonstrates the relative resistance of SBD.SE to UVB irradiation, as compared with bakuchiol. Both compounds were irradiated with UVB light and their HPLC-MS profile was compared to their respective non-irradiated controls. FIGS. 2, 3, 6, and 7 show HPLC chromatograms of UVB-irradiated (lower portions) and non-irradiated samples (upper portions) of bakuchiol (FIGS. 2 and 3) and SBD.SE (FIGS. 6 and 7) detected at 254 nm (FIGS. 2 and 6) and 230 nm (FIGS. 3 and 7). While bakuchiol disintegrates (demonstrated by the loss of the parent peak on FIG. 2, the shift of the new peak relative to the parent peak on FIG. 3 and the appearance of new molecular mass entities in FIG. 5 relative to FIG. 4. In contrast, SBD.SE shows no difference in mass of the peaks in the presence or absence of UVB light (compare FIG. 9 and FIG. 8). The comparison of the HPLC elution profiles (FIG. 6 and FIG. 7) reveals an additional peak in the UVB-irradiated SBD.SE, however, it appears to be a result of a rearrangement of hydrogen bonds rather than a covalent modification. SBD.SE is expected to have similar resistance to UVA irradiation.

Summary:

It can be seen that under UVB irradiation at 254 nm and 230 nm, SBD.SE is resistant to decomposition relative to bakuchiol by itself.

Example 5 Antimicrobial Activity of Meroterpene Esters

This example demonstrates the antimicrobial activity of meroterpene esters SBD.SE and SBD.FA. Serial dilutions of SBD.SE and SBD.FA were incubated with exponentially-growing planktonic *P. acnes* bacteria in oxygen-free atmosphere.

The MIC (minimal inhibitory concentration) for SBD.SE was determined to be about 30 μg/ml and for SBD.FA—about 60 μg/ml. It is reasonable to extend the coverage of these results to *P. acnes* and other bacteria growing in biofilms.

Summary:

SBD.SE and SBD.FA have been demonstrated antimicrobial activity against *P. acnes*.

Example 6: Reduced Irritation of SBD.SE Compared to Retinoic Acid

Tissue irritation is a common side effect of retinoids. It is mediated, at least in part, by retinoid interaction with retinoic acid receptors (RARs; Thacher S M, Vasudevan J, Chandraratna R A. Therapeutic applications for ligands of retinoid receptors. Curr Pharm Des. 2000 January; 6(1):25-58; Kambayashi H, Odake Y, Takada K, Funasaka Y, Ichihashi M, Kato S. N-retinoyl-D-glucosamine, a new retinoic acid agonist, mediates topical retinoid efficacy with no irritation on photoaged skin. Br J Dermatol. 2005 December; 153 Suppl 2:30-6). Here, we report that SBD.SE does not trigger transactivation of RAR up to 150 times higher concentration than ATRA-SBD.SE had no effect up to 50 μg/ml, while 0.3 μg/ml of ATRA achieved a 460% increase of RAR-mediated transcription in the Cignal RAR reporter assay from Qiagen. Therefore, it appears that SBD.SE has less potential for skin irritation than retinoic acid and other RAR-binding retinoids. The lack of irritation was further confirmed in the EpiOcular™ Eye Irritation Test (OCL-200-EIT) assay from (Mattek), where SBD.SE showed no statistically significant irritation in the reconstituted squamous epithelium model, while the positive control (methyl acetate) showed a substantial (36%) viability decrease as compared to water control (see Example 1).

Summary:

It has been demonstrated by a lack of transactivation of RAR and no statistically significant irritation in the reconstituted squamous epithelium model, that SBD.SE shows reduced irritation compared to retinoic acid.

Example 7: Lack of Phototoxicity of Meroterpene Esters

This example demonstrates lack of phototoxicity of meroterpene esters, such as SBD.FA and SBD.SE. Phototoxicity is defined as light-activated cytotoxicity. Many substances exhibit light-induced or light-aggravated cytotoxicity. The objective of this test was to determine whether SBD.SE and SBD.FA exhibit such light-activated toxicity. The protocol followed in this example was based on the OECD 432 Guidelines. Four 96 well plates were seeded with 3T3 cells (Sigma, St. Louis, Mo.; cat. 93061524-1VL) at 10,000 cells per well in DMEM supplemented with 10% iron-fortified calf serum, and grown overnight in humidified atmosphere at 37° C. in 5% CO2. Serial dilutions of SBD.SE and chlorpromazine (positive control) were added to 2 plates each. Cells were then returned to incubator for 1 h, afterward one plate with SBD.SE and one plate with chlorpromazine were placed in the dark at room temperature while the other 2 plates were irradiated through the lid with UVA Spectronics lamp at 5 J/cm2.

After UVA irradiation, medium with test materials was removed from both plates and replaced by fresh cell culture medium. Plates were returned to the incubator for 24 h, afterward the medium was removed, cells were rinsed with PBS and placed in Neutral Red medium at 50 μg/ml in which cells were incubated for 3 more hours. Wells were then washed with PBS and Neutral Red was extracted from cells with 1.0% Glacial Acetic Acid/50% Ethanol/49% H2O solution.

Following a 30-minute extraction with mixing, the absorbance of each well was measured at 570 nm with Molecular Devices SpectraMax® microplate spectrophotometer. P values were calculated using two-tailed Student's test and p=0.05 was set as borderline for statistical significance.

The result of this experiment showed that while the positive control (chlorpromazine) was found to be phototoxic (more than 10 times more toxic in the presence than in the absence of UVB light), SBD.FA and SBD.SE exhibited lack of significant cytotoxicity up to at least 100 μg/ml both in the absence and presence of UVB light).

Summary:

It has been demonstrated that SBD.FA and SBD.SE lack significant phototoxicity up to at least 100 μg/ml, either in the absence or presence of UVB irradiation.

Example 8: Beneficial Effect on Cytokine-Treated HEK Morphology

This example demonstrates the beneficial effect of SBDSE on the morphology of cytokine-treated HEK. Cytokines IL17A, IL22 and TNF-alpha were used to induce psoriatic phenotype in human skin substitutes, which resulted in morphologic changes, such as cell body enlargement, loss of cobblestone morphology and appearance of "fried egg" shaped cells. Adding 10 μg/ml of SBD.SE to cells prevents these changes and preserves a more non-cytokine-treated control-like cell shape. This is in agreement with the Example 3, showing that SBD.SE decreases cellular response to cytokine stimulus (Table 1).

Summary:

It has been demonstrated that addition of SBD.SE prevents morphologic changes normally induced by Cytokines IL17A, IL22 and TNF-alpha.

What is claimed is:

1. A composition comprising an esterified meroterpene, wherein
    the ester portion of the esterified meroterpene is selected from a ferulic ester, acetylsalicylic ester, salicylic ester, or a combination thereof; and
    the meroterpene portion of the esterified meroterpene is bakuchiol.

2. The composition of claim 1, wherein the esterified meroterpene has greater stability in the absence or presence of UVB light than bakuchiol, by itself.

3. The composition of claim 1, wherein the esterified meroterpene has lower cytotoxicity in the absence or presence of UVB light than bakuchiol, by itself.

4. The composition of claim 1, wherein the esterified meroterpene lacks significant cytotoxicity up to at least 100 µg/ml in the absence or presence of UVB light.

5. The composition of claim 1, wherein the esterified meroterpene inhibits the growth of *Propionibacterium acnes*.

6. The composition of claim 1, wherein the esterified meroterpene has a whiter color than bakuchiol, by itself.

7. The composition of claim 1, wherein the esterified meroterpene has antioxidant activity.

8. The composition of claim 1, wherein the ester portion is a salicylic ester.

9. The composition of claim 8, wherein the esterified meroterpene is at least 2 times less toxic to non-irradiated neonatal human dermal fibroblasts than bakuchiol, by itself.

10. The composition of claim 8, wherein the esterified meroterpene is at least 40 times less toxic to human epidermal keratinocytes than bakuchiol, by itself.

11. The composition of claim 1, wherein the ester portion is a ferulic ester.

12. The composition of claim 11, wherein the esterified meroterpene is at least 4 times less toxic to human epidermal keratinocytes or non-irradiated neonatal human dermal fibroblasts than bakuchiol, by itself.

13. The composition of claim 1, wherein the composition is a topical, pulmonary, intranasal, transoral, epidermal, transdermal, oral or parenteral composition.

14. The composition of claim 13, wherein the topical composition is a cream, lotion, serum, milk, ointment, patch, gel, film, patch or shampoo.

15. The composition of claim 13, wherein the pulmonary composition is an inhalable powder or aerosol.

16. The composition of claim 13, wherein the parenteral composition is an intravenous, intra-arterial, subcutaneous, intraperitoneal, an intramuscular injection, or an intramuscular infusion composition.

17. The composition of claim 1, wherein the composition comprises one or more skin protective ingredients selected from the group consisting of sunscreens, antioxidants, vitamins, anti-inflammatory agents, self-tanning agents, moisturizers, emollients, exfoliates, humectants, anti-cancer agents, or over the counter skin protectants.

18. The composition of claim 1, wherein the esterified meroterpene is formulated in pharmaceutically acceptable vehicle for injection, inhalation, transdermal, transbuccal or oral administration.

19. The composition of claim 1, wherein the composition is a nutrition supplement or functional food.

* * * * *